(12) United States Patent
Endo et al.

(10) Patent No.: US 8,927,597 B2
(45) Date of Patent: Jan. 6, 2015

(54) COMPOUNDS USEFUL IN THE SYNTHESIS OF HALICHONDRIN B ANALOGS

(71) Applicants: Atsushi Endo, Boston, MA (US); Charles E. Chase, Londonderry, NH (US); Francis G. Fang, Andover, MA (US)

(72) Inventors: Atsushi Endo, Boston, MA (US); Charles E. Chase, Londonderry, NH (US); Francis G. Fang, Andover, MA (US)

(73) Assignee: Eisai R&D Management Co., Ltd., Tokyo (JP)

( * ) Notice: Subject to any disclaimer, the term of this patent is extended or adjusted under 35 U.S.C. 154(b) by 38 days.

(21) Appl. No.: 13/735,516

(22) Filed: Jan. 7, 2013

(65) Prior Publication Data

US 2013/0123519 A1     May 16, 2013

Related U.S. Application Data

(62) Division of application No. 13/477,483, filed on May 22, 2012, now Pat. No. 8,350,067, which is a division of application No. 13/014,517, filed on Jan. 26, 2011, now Pat. No. 8,203,010.

(60) Provisional application No. 61/298,337, filed on Jan. 26, 2010.

(51) Int. Cl.
| | | |
|---|---|---|
| A61K 31/351 | (2006.01) | |
| C07D 407/00 | (2006.01) | |
| C07D 405/06 | (2006.01) | |
| C07D 407/06 | (2006.01) | |
| C07D 493/04 | (2006.01) | |
| C07D 405/12 | (2006.01) | |

(52) U.S. Cl.
CPC ............ *C07D 407/06* (2013.01); *C07D 405/06* (2013.01); *C07D 493/04* (2013.01); *C07D 405/12* (2013.01)
USPC .......................................... 514/451; 549/414

(58) Field of Classification Search
CPC .................................................... A61K 31/351
USPC .......................................... 549/414; 514/451
See application file for complete search history.

(56) References Cited

U.S. PATENT DOCUMENTS

| | | | |
|---|---|---|---|
| 5,338,865 A | 8/1994 | Kishi et al. | |
| 5,436,238 A | 7/1995 | Kishi et al. | |
| 6,214,865 B1 | 4/2001 | Littlefield et al. | |
| 6,365,759 B1 | 4/2002 | Littlefield et al. | |
| 6,469,182 B1 | 10/2002 | Littlefield et al. | |
| 6,653,341 B1 | 11/2003 | Littlefield et al. | |
| 7,470,720 B2 | 12/2008 | Littlefield et al. | |
| 7,982,060 B2 | 7/2011 | Austad et al. | |
| 8,093,410 B2 | 1/2012 | Chase et al. | |
| 8,148,554 B2 | 4/2012 | Seletsky et al. | |

(Continued)

FOREIGN PATENT DOCUMENTS

| | | |
|---|---|---|
| EP | 0572109 A1 | 12/1993 |
| WO | WO-93/17690 A1 | 9/1993 |

(Continued)

OTHER PUBLICATIONS

Aicher et al., "Total synthesis of halichondrin B and norhalichondrin B," J Am Chem Soc. 114(8):3162-64 (1992).

(Continued)

*Primary Examiner* — Rebecca Anderson
*Assistant Examiner* — Karen Cheng
(74) *Attorney, Agent, or Firm* — Clark & Elbing LLP

(57) ABSTRACT

In general, the invention features compounds useful for the synthesis of analogs of halichondrin B, such as eribulin or pharmaceutically acceptable salts thereof, e.g., eribulin mesylate. Exemplary compounds are of formula (I), (II), or (III):

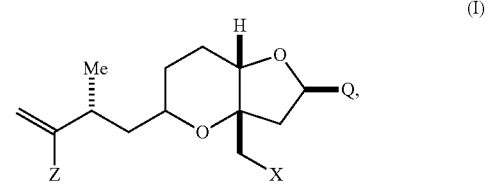

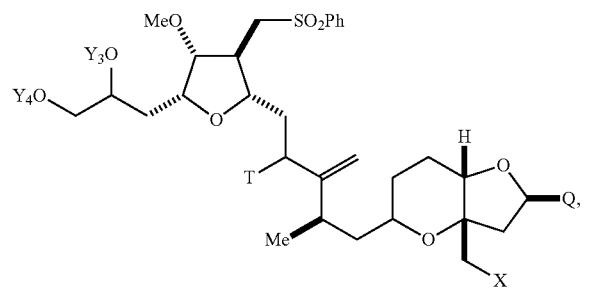

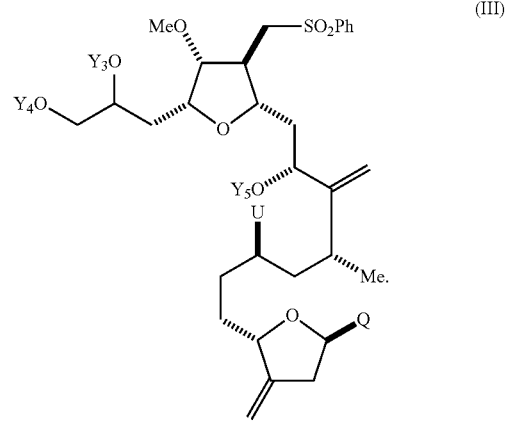

28 Claims, No Drawings

(56) References Cited

U.S. PATENT DOCUMENTS

| | | | |
|---|---|---|---|
| 8,203,010 | B2 | 6/2012 | Endo et al. |
| 8,350,067 | B2 | 1/2013 | Endo et al. |
| 8,445,701 | B2 | 5/2013 | Austad et al. |
| 2007/0244187 | A1 | 10/2007 | Austad et al. |
| 2009/0198074 | A1 | 8/2009 | Chase et al. |
| 2009/0203771 | A1 | 8/2009 | Inanaga et al. |
| 2011/0054194 | A1 | 3/2011 | Hu |
| 2011/0172446 | A1 | 7/2011 | Littlefield et al. |
| 2011/0184190 | A1 | 7/2011 | Endo et al. |
| 2012/0029213 | A1 | 2/2012 | Austad et al. |
| 2012/0095242 | A1 | 4/2012 | Chase et al. |
| 2012/0309988 | A1 | 12/2012 | Austad et al. |

FOREIGN PATENT DOCUMENTS

| | | |
|---|---|---|
| WO | WO-99/65894 A1 | 12/1999 |
| WO | WO-2005/118565 A1 | 12/2005 |
| WO | WO-2009/046308 A1 | 4/2009 |
| WO | WO-2009/064029 A1 | 5/2009 |
| WO | WO-2009/124237 A1 | 10/2009 |
| WO | WO-2011/094339 A1 | 8/2011 |

OTHER PUBLICATIONS

Aicher et al., "Synthetic studies towards halichondrins: synthesis of the C.27-C.38 segment," Tetrahedron Lett. 33(12):1549-52 (1992).

Alley et al. "Comparison of the relative efficacies and toxicities of Halichondrin B analogues," Proceedings of the AACR-NCI-EORTC Conference on Molecular Targets and Cancer Therapeutics. C230:257 (2005).

Anderson, "Developing processes for crystallization-induced asymmetric transformation," Org Process Res Dev. 9:800-13 (2005).

Austad et al., "Commercial manufacture of Halaven®: chemoselective transformations en route to structurally complex macrocyclic ketones," Synlett. 24 (2013). Supporting Information, (13 pages.).

Austad et al "Commercial manufacture of Halaven®: chemoselective transformations en route to structurally complex macrocyclic ketones," Synlett. 24:333-7 (2013).

Austad et al., "Process development of Halaven®: Synthesis of the C14-C35 fragment via iterative Nozaki-Hiyama-Kishi reaction—Williamson ether cyclization," Synlett. 24:327-32 (2013).

Bai et al., "Halichondrin B and Homohalichondrin B, marine natural products binding in the vinca domain of tubulin. Discovery of tubulin-based mechanism of action by analysis of differential cytotoxicity data," J Biol Chem 266(24):15882-89 (1991).

Bernet et al., "Carbocyclische verbindungen aus monosacchariden. Umsetzungen in der glucosereihe," Helv Chim Acta. 62:1990-2016 (1979).

Blanchette et al., "Horner-Wadsworth-Emmons reaction: use of lithium chloride and an amine for base-sensitive compounds," Tetrahedron Lett. 25(21):2183-6 (1984).

Burke et al., "Enantioselective synthesis of a Halichondrin B C(20)→C(36) precursor," Tetrahedron Lett. 36(39):7023-6 (1995).

Burke et al., "Synthesis of a C(22)→C(34) Halichondrin precursor via a double dioxanone-to-dihydropyran rearrangement," Tetrahedron Lett. 32(32):3961-4 (1991).

Burke et al., "Synthesis of a C(22)-C(34) Halichondrin B precursor via ring opening-double ring closing metathesis," J Org Chem. 63:8626-7 (1998).

Burke et al., "Synthetic studies toward complex polyether macrolides of marine origin," Spec Publ R Soc Chem. 198:(Anti-Infectives) 73-85 (1997).

Chase et al., "Process development of Halaven®: Synthesis of the C1-C13 fragment from D-(−)-Gulono-1, 4-lactone," Synlett. 24:323-326 (2013).

Chen et al., "Ni(II)/Cr(II)-mediated coupling reaction: An asymmetric process," J Org Chem. 60:5386-7 (1995).

Choi et al., "Assymmetric Ni(II)/Cr(II)-mediated coupling reaction: catalytic process," Org Lett.4(25):4435-8 (2002).

Choi et al., "Synthetic studies on the marine natural product Halichondrins," Pure Appl Chem. 75(1):1-17 (2003).

Cooper et al., "Total Synthesis of Halichondrin B from common sugars: an F-ring intermediate from D-glucose and efficient construction of the C1 to C21 segment," Tetrahedron Lett. 34(51):8193-8196 (1993).

Dabydeen et al. "Comparison of the activities of the truncated Halichondrin B analog NSC 707389 (E7389) with those of the parent compound and a proposed binding site on tubulin" Mol Pharmacol. 70(6):1866-75 (2006).

Dong et al. "New syntheses of E7389 C14-C35 and halichondrin C14-C38 building blocks: reductive cyclization and oxy-michael cyclization approaches," J Am Chem Soc. 131:15642-6 (2009).

Duan et al., "Synthetic studies on halichondrins: a new practical synthesis of the C.1-C.12 segment," Tetrahedron Lett. 34(47):7541-7544 (1993).

Flemming et al., "Nitrile anion cyclizations," Tetrahedron. 58:1-23 (2002).

Guo et al., "Toolbox approach to the search for effective ligands for catalytic asymmetric Cr-mediated coupling reactions," J Am Chem Soc. 131:15387-93 (2009).

Hirata et al., "Halichondrins—antitumor polyether macrolides from a marine sponge," Pure Appl Chem. 58(5):701-710 (1986).

Hori et al., "Efficient synthesis of 2,3-trans-tetrahydropyrans and oxepanes: rearrangement-ring expansion of cyclic ethers having a chloromethanesulfonate," Tetrahedron Lett. 40:2145-2148 (1999).

Horita et al., "Synthetic studies of Halichondrin B, an antitumor polyether macrolide isolated from a marine sponge. 8. Synthesis of the lactone part (C1-C36) via Horner-Emmons coupling between C1-C15 and C16-C36 fragments and yamaguchi lactonization," Tetrahedron Lett. 38(52):8965-8 (1997).

Horita et al., "Research on Anti-Tumor Active Site of Marine Source Natural Product, Halichondrin B.," International Congress Series, 1157 (Towards Natural Medicine Research in the 21st Century), 327-336 (1998).

Horita et al., "Synthetic studies of halichondrin B, an antitumor polyether macrolide isolated from a marine sponge. 2. Efficient synthesis of C16-C26 fragments via construction of the D ring by a highly stereocontrolled Iodoetherification," Synlett. 40-43 (1994).

Horita et al., "Synthetic studies of Halichondrin B, an antitumor polyether macrolide isolated from a marine sponge. 3. Synthesis of C27-C36 subunit via completely stereoselective C-glycosylation to the F ring," Synlett. 43-45 (1994).

Horita et al., "Synthetic studies of Halichondrin B, an antitumor polyether macrolide isolated from a marine sponge. 7. Synthesis of two C27-C36 units via construction of the F ring and completely stereoselective C-glycosylation using mixed lewis acids," Chem Pharm Bull. 45(10):1558-72 (1997).

Horita et al., "Synthetic studies on Halichondrin B, an antitumor polyether macrolide issolated from a marine sponge. 9. Synthesis of the C16-C36 unit via stereoselective construction of the D and E rings," Chem Pharm Bull. 46(8):1199-1216 (1998).

Horita et al., "Synthetic study of a highly antitumorigenic marine phytochemical, Halichondrin B," *Phytochemicals and Phytopharmaceuticals*, Fereidoon Shahidi and Chi-Tang Ho, 386-397 (2000).

Jackson et al., "A total synthesis of norhalichondrin B," Angew Chem Int Ed. 48:2346-2350 (2009).

Jackson et al., "The halichondrins and E7389," Chem Rev 109:3044-3079 (2009).

Jiang et al., "A novel route to the F-ring of Halichondrin B. Diastereoselection in Pd(0)-mediated meso and C2 diol desymmetrization," Org Lett., 4(20):3411-3414 (2002).

Jiang et al., "A practical synthesis of the F-ring of Halichondrin B via ozonolytic desymmetrization of a C2-symmetric dihydroxycyclohexene," J Org Chem. 68:1150-1153 (2003).

Kim et al., "New syntheses of E7389 C14-C35 and Halichondrin C14-C38 building blocks: double-inversion approach" J Am Chem Soc. 131:15636-41 (2009).

Kurosu et al., "Fe/Cr- and Co/Cr-mediated catalytic asymmetric 2-Haloallylations of aldehydes," J Am Chem Soc. 126:12248-9 (2004).

(56) References Cited

OTHER PUBLICATIONS

Mattocks, "371. Novel reactions of some alpha-acyloxy acid chlorides," J Chem Soc. 1918-30 (1964).
Mattocks, "932. Novel reactions of some alpha-acyloxy-acid halides," J Chem Soc. 4840-5 (1964).
Mitsunobu, "The use of diethyl azodicarboxylate and triphenylphosphine in synthesis and transformation of natural products," Synthesis. 1-28 (1981).
Newman, "Drug evaluation: eribulin, a simplified ketone analog of the tubulin inhibitor Halichondrin B, for the potential treatment of cancer," Curr Opin Invest Drugs. 8:1057-1066 (2007).
Aicher, Thomas Daniel, Thesis, Chapter 4, "Synthetic studies towards halichondrin B," Doctor of Philosophy in Chemistry, Harvard Universary, 35-54 (1990).
Sakamoto et al., "Stereoselective ring expansion via bicyclooxonium Ion. A novel approach to oxocanes," Org Lett. 4(5):675-678 (2002).
Schreiber, "Hydrogen transfer from tertiary amines to trifluoroacetic anhydride," Tetrahedron Lett. 21:1027-1030 (1980).
Seletsky et al. "Structurally simplified macrolactone analogues of halichondrin B," Bioorg Med Chem Lett. 14:5547-50 (2004).
Stamos et al., "A mild preparation of vinyliodides from vinylsilanes," Tetrahedron Lett. 37(48): 8647-8650 (1996).
Stamos et al., "New synthetic route to the C.14-C.38 segment of Halichondrins," J Org Chem. 62:7552-7553 (1997).
Stamos et al., "Synthetic studies on Halichondrins: a practical synthesis of the C.1-C.13 segment," Tetrahedron Lett. 37(48): 8643-8646 (1996).
Stamos, D.P., et al., "Ni(II)/Cr(II)-mediated coupling reaction: beneficial effects of 4-tert-butylpyridine as an additive and development of new and improved workup procedures," Tetrahedron Lett., 38(36):6355-6358 (1997).
Tokunaga et al., "Asymmetric catalysis with water: efficient kinetic resolution of terminal epoxides by means of catalytic hydrolysis," Science. 277:936-938 (1997).
Towle et al. "Halichondrin B macrocyclic ketone analog E7389: medicinal chemistry repair of lactone ester instability generated during structural simplification to clinical Candidate" Annual Meeting of the American Association for Cancer Research, Apr. 6-10, 2002, 5721.
Towle et al. "In vitro and in vivo anticancer activities of synthetic macrocyclic ketone analogues of Halichondrin B" Cancer Res. 61:1013-1021 (2001).
Uemura et al., "Norhalichondrin A: an antitumor polyether macrolide from a marine sponge," J Am Chem Soc. 107:4796-4798 (1985).
Vahdat et al., "Phase II study of eribulin mesylate, a Halichondrin B analog, in patients with metastatic breast cancer previously treated with an anthracycline and a taxane," J Clin Oncol. 27(18):2954-2961 (2009).
Wan et al., "Asymmetric Ni(II)/Cr(II)-mediated coupling reaction: Stoichiometric process," Org Lett. 4(25):4431-4434 (2002).
Wang et al. "Structure-activity relationships of Halichondrin B analogues: Modifications at C.30-C.38" Bioorg Med Chem Lett. 10:1029-1032 (2000).
Xie et al., "Synthesis of the C20-C26 building block of Halichondrins via a regiospecific and stereoselective SN2' reaction," Org Lett. 4(25): 4427-4429 (2002).
Yang et al., "Second generation synthesis of C27-C35 building block of E7389, a synthetic Halichondrin analogue," Org Lett. 11(20): 4516-4519 (2009).
Yu et al., "New synthetic route to the C.14-C.21 fragment of Halichondrin B," Book of Abstracts. 219th ACS National Meeting, San Francisco, CA, Mar. 26-30 (2000).
Yu et al., "Discovery of E7389 a fully synthetic macrocyclic ketone analog of Halichondrin B," *Anticancer Agents from Natural Product*; CRC Press: Boca Raton, FL, 241-265. (2005).
Zheng et al., "Macrocyclic ketone analogues of Halichondrin B," Bioorg Med Chem Lett. 14: 5551-5554 (2004).
Zheng, W. et al. "Synthetic macrocyclic ketone analogs of halichondrin B: structure-activity relationships" Proceedings of the American Association for Cancer Research, 41:301(#1915) (2000).
Examination Report for European Patent Application No. 11 702 900.9, dated Jul. 4, 2013 (5 pages).
International Search Report from International Application No. PCT/US2011/022611, mailed May 17, 2011.
International Search Report and Written Opinion from International Application No. PCT/US2011/022611 mailed May 17, 2011.

COMPOUNDS USEFUL IN THE SYNTHESIS OF HALICHONDRIN B ANALOGS

CROSS-REFERENCE TO RELATED APPLICATIONS

This application is a divisional of U.S. application Ser. No. 13/477,483, filed May 22, 2012, which is divisional of U.S. application Ser. No. 13/014,517, filed Jan. 26, 2011, which claims benefit of U.S. Provisional Application No. 61/298,337, filed on Jan. 26, 2010, each of which is hereby incorporated by reference.

BACKGROUND OF THE INVENTION

The invention relates to compounds useful in the synthesis of analogs of halichondrin B.

Eribulin mesylate, a nontaxane microtubule dynamics inhibitor, is a structurally simplified, synthetic analog of the marine natural product halichondrin B. Methods for the synthesis of eribulin and other halichondrin B analogs are described in International Publication No. WO 2005/118565 and U.S. Pat. No. 6,214,865. New intermediates for the synthesis of halichondrin B analogs, in particular eribulin, are desirable.

SUMMARY OF THE INVENTION

In general, the invention features compounds useful for the synthesis of analogs of halichondrin B, such as eribulin, including pharmaceutically acceptable salts thereof, e.g., eribulin mesylate.

In one aspect, the invention provides a compound having the formula (I):

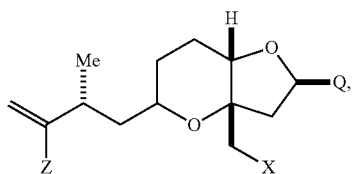

wherein X is halogen or oxo; Z is a leaving group; Q is —C(O)H, —CH=CHC(O)OY$_1$, —C(R)H(CH$_2$)$_n$OY$_1$, or —C(R)HCH$_2$C(O)OY$_1$; R is H or —OY$_2$; Y$_1$ and Y$_2$ are each independently H or a hydroxyl protecting group; and n is 1 or 2. Exemplary compounds have the formula (Ia):

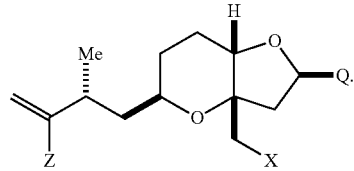

In particular embodiments, Q is —(CH$_2$)$_3$OY$_1$, for example wherein Y$_1$, together with the oxygen to which it is bound, is an ester, carbonate, carbamate, sulfonate, or ether hydroxyl protecting group. For example, Y$_1$ is pivaloyl, acetyl, benzoyl, p-bromobenzoyl, p-methoxybenzoyl, 1-naphthoyl, 2-naphthoyl, o-phthaloyl, benzyl, p-methoxybenzyl, triphenylmethyl, tri(C1-C6 alkyl)silyl, tri(C6-C10 aryl or C1-C6 heteroaryl)silyl, di(C6-C10 aryl or C1-C6 heteroaryl)(C1-C6 alkyl)silyl, or (C6-C10 aryl or C1-C6 heteroaryl)di(C1-C6 alkyl)silyl.

In other embodiments, X is halogen, and/or Z is halogen or (C1-C6)alkylsulfonate (such as triflate, iodide, or bromide).

In other embodiments, the compounds are of the formula (Ib):

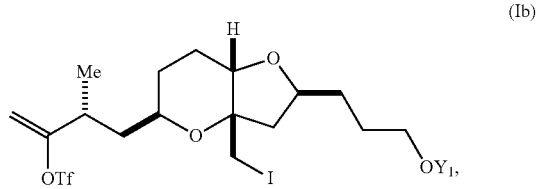

wherein Y$_1$ is H, pivaloyl, benzoyl, p-bromobenzoyl, 1-naphthoyl, 2-naphthoyl, p-methoxybenzoyl, or o-phthaloyl or a salt thereof.

In certain embodiments, Q is —C(O)H, —CH=CHC(O)OY$_1$, or —C(R)HCH$_2$C(O)OY$_1$; X is bromo, chloro, fluoro, or oxo; or Z is halogen, C1-C12 alkoxy, C2-C12 alkylsulfonate, C2-C12 alkenylsulfonate, carbocyclic C6-C20 arylsulfonate, C4-C19 heteroarylsulfonate, monocyclic C1-C6 heteroarylsulfonate, (C6-C15)aryl(C1-C6)alkylsulfonate, (C4-C19)heteroaryl(C1-C6)alkylsulfonate, (C1-C6)heteroaryl(C1-C6)alkylsulfonate, or diazonium; or combinations thereof.

In other embodiments, when Q is —(CH$_2$)$_3$OY$_1$, Z is triflate, and X is iodide, Y$_1$ is not pivaloyl; when Q is —(CH$_2$)$_3$OY$_1$, Y$_1$ is pivaloyl, and Z is triflate, X is not iodide; or when Q is —(CH$_2$)$_3$OY$_1$, Y$_1$ is pivaloyl, and X is iodide, Z is not triflate. Alternatively, when Z is triflate, and X is iodide, Q is not —(CH$_2$)$_3$OY$_1$.

In another aspect, the invention features compounds having the formula (II):

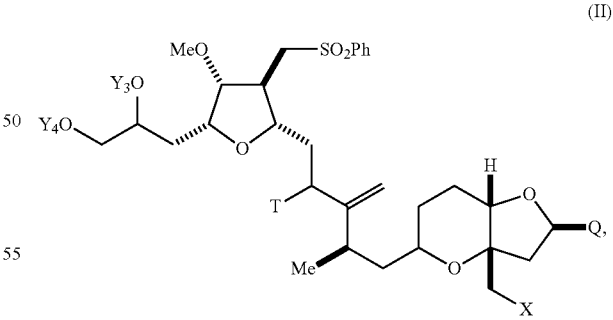

wherein X is halogen or oxo; Q is —C(O)H, —CH=CHC(O)OY$_1$, —C(R)H(CH$_2$)$_n$OY$_1$, or —C(R)HCH$_2$C(O)OY$_1$; R is H or —OY$_2$; n is 1 or 2; Y$_1$, Y$_2$, Y$_3$, and Y$_4$ are each independently H or a hydroxyl protecting group; T is oxo or —OY$_5$; and Y$_5$ is H or a hydroxyl protecting group, or Y$_5$, together with the oxygen atom to which it is bound, is a leaving group. Exemplary compounds have the formula:

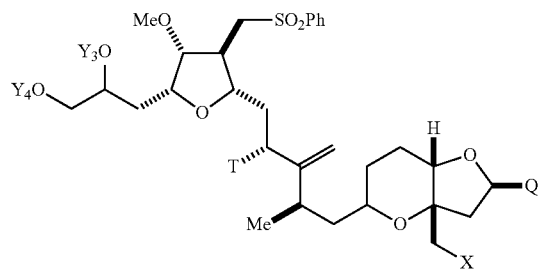

(IIa)

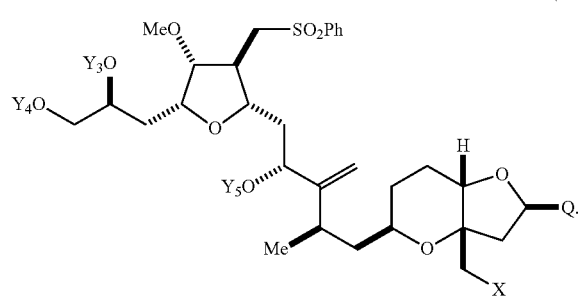

(IIb)

In particular embodiments, Q is —(CH$_2$)$_3$OY$_1$. In these embodiments, Y$_1$, together with the oxygen atom to which it is bound, can be an ester, carbonate, carbamate, sulfonate, or ether hydroxyl protecting group; Y$_3$ and Y$_4$ can each, independently and together with the oxygen atom to which it is bound, be an ester, carbonate, carbamate, sulfonate, or ether hydroxyl protecting group, or Y$_3$ and Y$_4$ together with the oxygen atoms to which they are bound can be a cyclic carbonate, cyclic boronate, acetal, ketal, or cyclic silylene hydroxyl protecting group or 1,1,3,3-tetraisopropylsiloxanediyl; T can be —OY$_5$; and/or Y$_5$, together with the oxygen atom to which it is bound, can be an ester, carbonate, carbamate, sulfonate, or ether hydroxyl protecting group. In these embodiments, Y$_1$ is, for example, pivaloyl, acetyl, benzoyl, p-bromobenzoyl, p-methoxybenzoyl, 1-naphthoyl, 2-naphthoyl, o-phthaloyl, benzyl, p-methoxybenzyl, triphenylmethyl, tri(C1-C6 alkyl)silyl, tri(C6-C10 aryl or C1-C6 heteroaryl)silyl, di(C6-C10 aryl or C1-C6 heteroaryl)(C1-C6 alkyl)silyl, or (C6-C10 aryl or C1-C6 heteroaryl)di(C1-C6 alkyl)silyl; Y$_3$ and Y$_4$ are, for example, each independently tri(C1-C6 alkyl)silyl, tri(C6-C10 aryl or C1-C6 heteroaryl)silyl, di(C6-C10 aryl or C1-C6 heteroaryl)(C1-C6 alkyl)silyl, or (C6-C10 aryl or C1-C6 heteroaryl)di(C1-C6 alkyl)silyl, or Y$_3$ and Y$_4$ are together di(C1-C6alkyl)silylene; and/or Y$_5$ is, for example, acetyl, benzoyl, p-bromobenzoyl, p-methoxybenzoyl, 1-naphthoyl, 2-naphthoyl, or o-phthaloyl.

In other embodiments, X is halogen. These compounds can also have the formula (IIc):

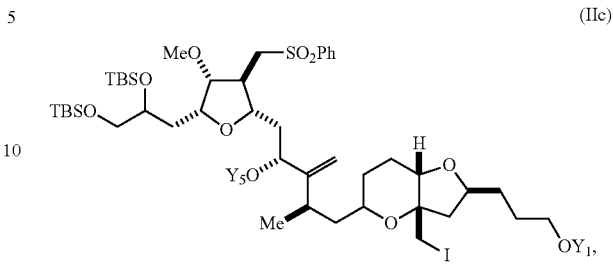

(IIc)

wherein Y$_1$ and Y$_5$ are as follows:

| Y$_1$ | Y$_5$ |
|---|---|
| H | H |
| benzoyl | benzoyl |
| p-bromobenzoyl | p-bromobenzoyl |
| pivaloyl | H |
| pivaloyl | acetyl |
| pivaloyl | benzoyl |
| 2-naphthoyl | H |
| 2-naphthoyl | 2-naphthoyl |
| 1-naphthoyl | H |
| 1-naphthoyl | 1-naphthoyl |
| p-methoxybenzoyl | H |
| p-methoxybenzoyl | p-methoxybenzoyl |
| o-phthaloyl or salt thereof | H |

A specific compound is

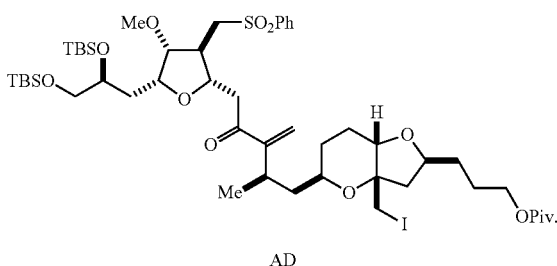

AD

In another embodiment, the invention features a compound having the formula (III):

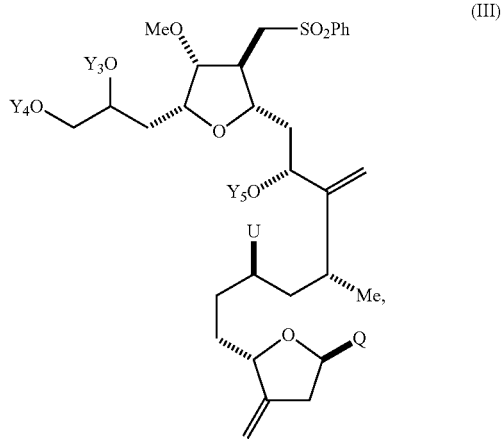

(III)

wherein Q is —C(O)H, —CH═CHC(O)OY$_1$, —C(R)H(CH$_2$)$_n$OY$_1$, or —C(R)HCH$_2$C(O)OY$_1$; R is H or —OY$_2$; n is 1 or 2; Y$_1$, Y$_2$, Y$_3$, and Y$_4$ are each independently H or a hydroxyl protecting group; U is halogen or —OY$_6$; Y$_5$ is H or a hydroxyl protecting group or Y$_5$, together with the oxygen atom to which it is bound, is a leaving group; and Y$_6$ is H or a hydroxyl protecting group or Y$_6$, together with the oxygen atom to which it is bound, is a leaving group, provided that when Q is —(CH$_2$)$_3$OY$_1$, U is —OY$_6$, wherein —OY$_6$ is a leaving group, and Y$_1$, Y$_3$, and Y$_4$ are protecting groups, Y$_5$ is not H. Exemplary compounds have the formula (IIIa):

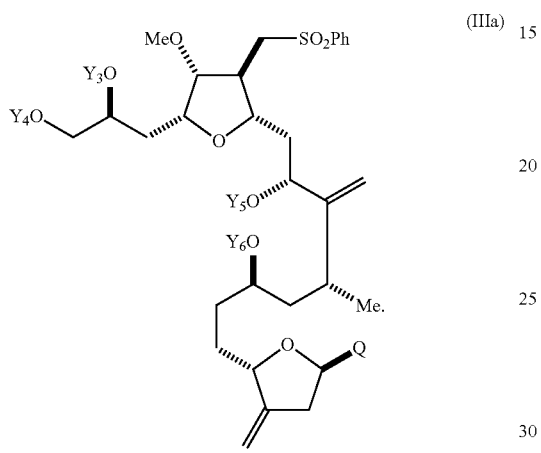

In particular embodiments, Q is —(CH$_2$)$_3$OY$_1$. In these embodiments, Y$_1$, together with the oxygen atom to which it is bound, is, for example, an ester, carbonate, carbamate, sulfonate, or ether hydroxyl protecting group; each of Y$_3$ and Y$_4$ is, for example, independently and together with the oxygen atom to which it is bound, an ester, carbonate, carbamate, sulfonate, or ether hydroxyl protecting group, or Y$_3$ and Y$_4$ together with the oxygen atoms to which they are bound are, for example, a cyclic carbonate, cyclic boronate, acetal, ketal, or cyclic silylene hydroxyl protecting group or 1,1,3,3-tetraisopropylsiloxanediyl; and/or Y$_5$, together with the oxygen atom to which it is bound, is, for example, an ester, carbonate, carbamate, sulfonate, or ether hydroxyl protecting group. In specific examples, Y$_1$ is pivaloyl, acetyl, benzoyl, p-bromobenzoyl, p-methoxybenzoyl, 1-naphthoyl, 2-naphthoyl, o-phthaloyl, benzyl, p-methoxybenzyl, triphenylmethyl, tri(C1-C6 alkyl)silyl, tri(C6-C10 aryl or C1-C6 heteroaryl)silyl, di(C6-C10 aryl or C1-C6 heteroaryl)(C1-C6 alkyl)silyl, or (C6-C10 aryl or C1-C6 heteroaryl)di(C1-C6 alkyl)silyl; Y$_3$ and Y$_4$ are each independently tri(C1-C6 alkyl)silyl, tri(C6-C10 aryl or C1-C6 heteroaryl)silyl, di(C6-C10 aryl or C1-C6 heteroaryl)(C1-C6 alkyl)silyl, or (C6-C10 aryl or C1-C6 heteroaryl)di(C1-C6 alkyl)silyl, or Y$_3$ and Y$_4$ are together di(C1-C6)alkylsilylene; and/or Y$_5$ is acetyl, benzoyl, p-bromobenzoyl, p-methoxybenzoyl, 1-naphthoyl, 2-naphthoyl, or o-phthaloyl.

In other embodiments, Y$_5$ is H or a hydroxyl protecting group; Y$_6$ is H; or —OY$_6$ is a leaving group, such as (C1-C6)alkylsulfonate, (C6-C10 aryl or C1-C6 heteroaryl)sulfonate, (C6-C15)aryl(C1-C6)alkylsulfonate, or (C1-C6)heteroaryl(C1-C6)alkylsulfonate. Specific leaving groups include mesylate, toluenesulfonate, isopropylsulfonate, phenylsulfonate, or benzylsulfonate.

A specific example has the formula:

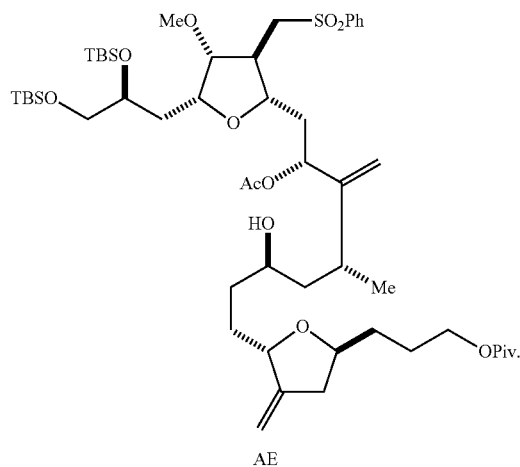

AE

Additional compounds of the invention are described herein.

The invention further features use of the compounds of the invention, e.g., Compounds E-AM, in the manufacture of ER-804028 and analogs of halichondrin B, such as eribulin, or a pharmaceutically acceptable salt thereof, e.g., eribulin mesylate.

In one aspect, the invention features a method of synthesizing ER-804028 by (i) reacting a compound having the formula (I):

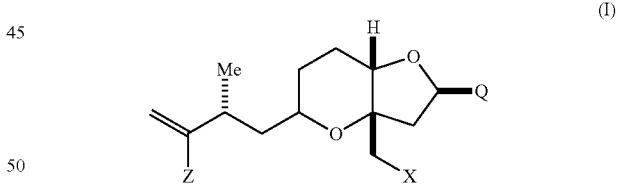

with a compound having the formula (IV):

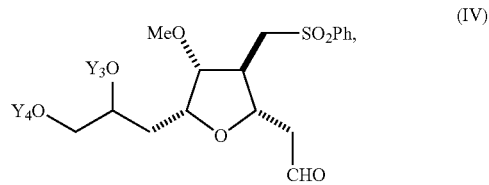

wherein Y$_3$, and Y$_4$, are each independently H or a hydroxyl protecting group, under Nozaki-Hiyama-Kishi (NHK) coupling conditions to produce a compound of formula (II):

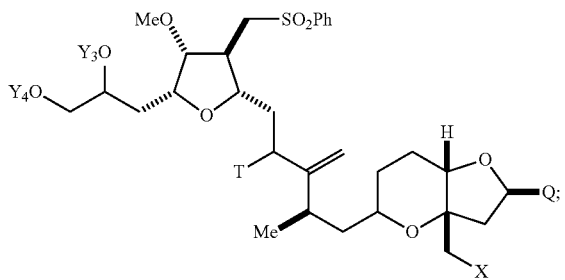

(ii) reacting the product of step (i) under Vasella fragmentation conditions to produce a compound of formula (III):

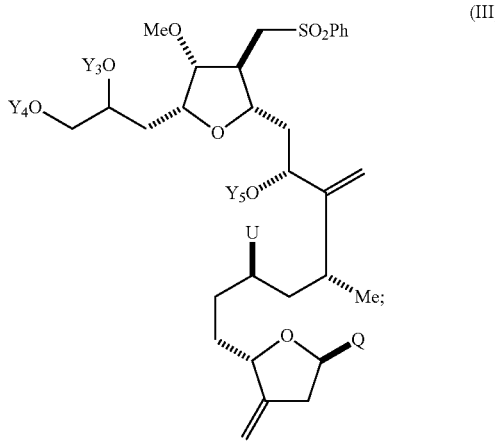

and
(iii) reacting the product of step (ii) under conditions for intramolecular Williamson etherification to produce ER-804028:

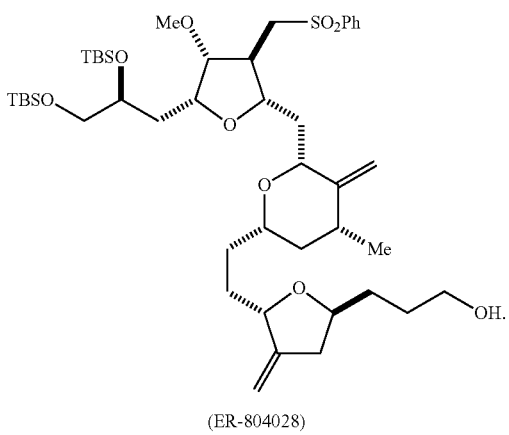

(ER-804028)

Asymmetric or chiral centers exist in the compounds of the invention. The present invention includes the various stereoisomers of the compounds and mixtures thereof, unless otherwise specified. Individual stereoisomers of the compounds of the present invention are prepared synthetically from commercially available starting materials that contain asymmetric or chiral centers or by preparation of mixtures of compounds followed by resolution as is well known in the art. These methods of resolution are exemplified by direct separation of the mixture of diastereomers on chiral chromatographic columns or by chiral HPLC methods. Methods of chiral separation have been described previously (GB. Cox (ed.) in *Preparative Enantioselective Chromatography*, 2005, Blackwell Publishing) Alternatively, chiral compounds can be prepared by an asymmetric synthesis that favors the preparation of one diastereomer over another. Geometric isomers may also exist in the compounds of the present invention. The present invention includes the various geometric isomers and mixtures thereof resulting from the arrangement of substituents around a carbon-carbon double bond, such as isomers of the Z or E configuration. It is also recognized that for structures in which tautomeric forms are possible, the description of one tautomeric form is equivalent to the description of both, unless otherwise specified. In certain embodiments, a diastereomer of a compound of the invention is present in a mixture at a ratio of 10:1, 20:1, 30:1, 50:1, or greater as compared to other diastereomers.

Compounds useful in the invention may be isotopically labeled compounds. Useful isotopes include hydrogen, carbon, nitrogen, and oxygen (e.g., $^2H$, $^3H$, $^{13}C$, $^{14}C$, $^{15}N$, $^{18}O$, and $^{17}O$). Isotopically-labeled compounds can be prepared by synthesizing a compound using a readily available isotopically-labeled reagent in place of a non-isotopically-labeled reagent.

For any of the following chemical definitions, a number following an atomic symbol indicates that total number of atoms of that element that are present in a particular chemical moiety. As will be understood, other atoms, such as hydrogen atoms, or substituent groups, as described herein, may be present, as necessary, to satisfy the valences of the atoms. For example, an unsubstituted C2 alkyl group has the formula —CH$_2$CH$_3$. When used with the groups defined herein, a reference to the number of carbon atoms includes the divalent carbon in acetal and ketal groups but does not include the carbonyl carbon in acyl, ester, carbonate, or carbamate groups. A reference to the number of oxygen, nitrogen, or sulfur atoms in a heteroaryl group only includes those atoms that form a part of a heterocyclic ring.

By "acetal" is meant >CHR (or —CHR—), wherein R is H, alkyl, alkenyl, aryl, or arylalkyl.

By "acyl" is meant —C(O)R, wherein R is H, alkyl, alkenyl, aryl, or arylalkyl. In exemplary acyl groups, R is H, C1-C12 alkyl (e.g., C1-C8, C1-C6, C1-C4, C2-C7, C3-C12, and C3-C6 alkyl), C2-C12 alkenyl (e.g., C2-C8, C2-C6, C2-C4, C3-C12, and C3-C6 alkenyl), C6-C20 aryl (e.g., C6-C15, C6-C10, C8-C20, and C8-C15 aryl), monocyclic C1-C6 heteroaryl (e.g., monocyclic C1-C4 and C2-C6 heteroaryl), C4-C19 heteroaryl (e.g., C4-C10 heteroaryl), (C6-C15)aryl(C1-C6)alkyl, (C1-C6)heteroaryl(C1-C6)alkyl, or (C4-C19)heteroaryl(C1-C6)alkyl. As defined herein, any heteroaryl group present in an acyl group has from 1 to 4 heteroatoms selected independently from O, N, and S.

By "alkyl" is meant a straight or branched chain saturated cyclic (i.e., cycloalkyl) or acyclic hydrocarbon group of from 1 to 12 carbons, unless otherwise specified. Exemplary alkyl groups include C1-C8, C1-C6, C1-C4, C2-C7, C3-C12, and C3-C6 alkyl. Specific examples include methyl, ethyl, 1-propyl, 2-propyl, 2-methyl-1-propyl, 1-butyl, 2-butyl, and the like. Unless otherwise noted, alkyl groups, used in any context herein, are optionally substituted with halogen, alkoxy, aryloxy, arylalkyloxy, oxo, alkylthio, alkylenedithio, alkylamino, [alkenyl]alkylamino, [aryl]alkylamino, [arylalkyl]alkylamino, dialkylamino, silyl, sulfonyl, cyano, nitro, carboxyl, or azido.

By "alkylamino" is meant —NHR, wherein R is alkyl. By "[alkenyl]alkylamino" is meant —NRR', wherein R is alkyl, and R' is alkenyl. By "[aryl]alkylamino" is meant —NRR', wherein R is alkyl, and R' is aryl. By "[arylalkyl]alkylamino" is meant —NRR', wherein R is alkyl, and R' is arylalkyl. By "dialkylamino" is meant —NR$_2$, wherein each R is alkyl, selected independently.

By "alkylene" is meant a divalent alkyl group. Alkylene groups, used in any context herein, are optionally substituted in the same manner as alkyl groups. For example, a C1 alkylene group is —CH$_2$—.

By "alkylenedithio" is meant —S-alkylene-S—.

By "alkylthio" is meant —SR, wherein R is alkyl.

By "alkenyl" is meant a straight or branched chain cyclic or acyclic hydrocarbon group of, unless otherwise specified, from 2 to 12 carbons and containing one or more carbon-carbon double bonds. Exemplary alkenyl groups include C2-C8, C2-C7, C2-C6, C2-C4, C3-C12, and C3-C6 alkenyl. Specific examples include ethenyl (i.e., vinyl), 1-propenyl, 2-propenyl (i.e., allyl), 2-methyl-1-propenyl, 1-butenyl, 2-butenyl (i.e., crotyl), and the like. Alkenyl groups, used in any context herein, are optionally substituted in the same manner as alkyl groups. Alkenyl groups, used in any context herein, may also be substituted with an aryl group.

By "alkoxy" is meant —OR, wherein R is alkyl.

By "aryl" is meant a monocyclic or multicyclic ring system having one or more aromatic rings, wherein the ring system is carbocyclic or heterocyclic. Heterocyclic aryl groups are also referred to as heteroaryl groups. A heteroaryl group includes 1 to 4 atoms selected independently from O, N, and S. Exemplary carbocyclic aryl groups include C6-C20, C6-C15, C6-C10, C8-C20, and C8-C15 aryl. A preferred aryl group is a C6-10 aryl group. Specific examples of carbocyclic aryl groups include phenyl, indanyl, indenyl, naphthyl, phenanthryl, anthracyl, and fluorenyl. Exemplary heteroaryl groups include monocylic rings having from 1 to 4 heteroatoms selected independently from O, N, and S and from 1 to 6 carbons (e.g., C1-C6, C1-C4, and C2-C6). Monocyclic heteroaryl groups preferably include from 5 to 9 ring members. Other heteroaryl groups preferably include from 4 to 19 carbon atoms (e.g., C4-C10). Specific examples of heteroaryl groups include pyridinyl, quinolinyl, dihydroquinolinyl, isoquinolinyl, quinazolinyl, dihydroquinazolyl, and tetrahydroquinazolyl. Unless otherwise specified, aryl groups, used in any context herein, are optionally substituted with alkyl, alkenyl, aryl, arylalkyl, halogen, alkoxy, aryloxy, arylalkyloxy, oxo, alkylthio, alkylenedithio, alkylamino, [alkenyl]alkylamino, [aryl]alkylamino, [arylalkyl]alkylamino, dialkylamino, silyl, sulfonyl, cyano, nitro, carboxyl, or azido.

By "arylalkyl" is meant —R'R", wherein R' is alkylene, and R" is aryl.

By "arylalkyloxy" is meant —OR, wherein R is arylalkyl.

By "aryloxy" is meant —OR, wherein R is aryl.

By "carbamate" is meant —OC(O)NR$_2$, wherein each R is independently H, alkyl, alkenyl, aryl, or arylalkyl.

By "carbonate" is meant —OC(O)OR, wherein R is alkyl, alkenyl, aryl, or arylalkyl.

By "carboxyl" is meant —C(O)OH, in free acid, ionized, or salt form.

By "cyclic boronate" is meant —OBRO—, wherein R is alkyl, alkenyl, aryl, arylalkyl, alkoxy, or 2,6-diacetamidophenyl.

By "cyclic carbonate" is meant —OC(O)O—.

By "cyclic silylene" is meant —OSiR$_2$O—, wherein each R is independently alkyl, alkenyl, aryl, arylalkyl, or alkoxy.

By "dialkylsilylene" is meant a cyclic silylene, wherein each R is alkyl.

By "ester" is meant —OC(O)R, where —C(O)R is an acyl group, as defined herein, that is bound to the oxygen atom of a protected hydroxyl, as defined below.

By "ether" is meant —OR, wherein R is alkyl, alkenyl, arylalkyl, silyl, or 2-tetrahydropyranyl.

By "halogen" is meant fluoro, chloro, bromo, or iodo.

By "ketal" is meant >CR$_2$ (or —CR$_2$—), wherein each R is independently alkyl, alkenyl, aryl, or arylalkyl, or both R groups are together alkylene.

By "oxo" or (O) is meant =O.

By "silyl" is meant —SiR$_3$, wherein each R is independently alkyl, alkenyl, aryl, or arylalkyl. Examples of silyl groups include tri(C1-C6 alkyl)silyl, tri(C6-C10 aryl or C1-C6 heteroaryl)silyl, di(C6-C10 aryl or C1-C6 heteroaryl)(C1-C6 alkyl)silyl, and (C6-C10 aryl or C1-C6 heteroaryl)di(C1-C6 alkyl)silyl. It will be understood that, when a silyl group includes two or more alkyl, alkenyl, aryl, heteroaryl, or arylalkyl groups, these groups are independently selected. As defined herein, any heteroaryl group present in a silyl group has from 1 to 4 heteroatoms selected independently from O, N, and S.

By "sulfonate" is meant —OS(O)$_2$R, wherein R is alkyl, alkenyl, aryl, or arylalkyl. In exemplary sulfonates, R is C1-C12 alkyl (e.g., C1-C8, C1-C6, C1-C4, C2-C7, C3-C12, and C3-C6 alkyl), C2-C12 alkenyl (e.g., C2-C8, C2-C6, C2-C4, C3-C12, and C3-C6 alkenyl), carbocyclic C6-C20 aryl (e.g., C6-C15, C6-C10, C8-C20, and C8-C15 aryl), monocyclic C1-C6 heteroaryl (e.g., C1-C4 and C2-C6 heteroaryl), C4-C19 heteroaryl (e.g., C4-C10 heteroaryl), (C6-C15)aryl(C1-C6)alkyl, (C4-C19)heteroaryl(C1-C6)alkyl, or (C1-C6)heteroaryl(C1-C6)alkyl. As defined herein, any heteroaryl group present in a sulfonate group has from 1 to 4 heteroatoms selected independently from O, N, and S.

By "sulfonyl" is meant —S(O)$_2$R, wherein R is alkyl, alkenyl, aryl, arylalkyl, or silyl. Preferred R groups for sulfonyl are the same as those described above for sulfonates.

By "hydroxyl protecting group" is meant any group capable of protecting the oxygen atom to which it is attached from reacting or bonding. Hydroxyl protecting groups are known in the art, e.g., as described in Wuts, *Greene's Protective Groups in Organic Synthesis*, Wiley-Interscience, 4$^{th}$ Edition, 2006. Exemplary protecting groups (with the oxygen atom to which they are attached) are independently selected from esters, carbonates, carbamates, sulfonates, and ethers.

In exemplary ester hydroxyl protecting groups, R of the acyl group is C1-C12 alkyl (e.g., C1-C8, C1-C6, C1-C4, C2-C7, C3-C12, and C3-C6 alkyl), C2-C12 alkenyl (e.g., C2-C8, C2-C6, C2-C4, C3-C12, and C3-C6 alkenyl), carbocyclic C6-C20 aryl (e.g., C6-C15, C6-C10, C8-C20, and C8-C15 aryl), monocyclic C1-C6 heteroaryl (e.g., C1-C4 and C2-C6 heteroaryl), C4-C19 heteroaryl (e.g., C4-C10 heteroaryl), (C6-C15)aryl(C1-C6)alkyl, (C4-C19)heteroaryl(C1-C6)alkyl, or (C1-C6)heteroaryl(C1-C6)alkyl. Specific examples of acyl groups for use in esters include formyl, benzoylformyl, acetyl (e.g., unsubstituted or chloroacetyl, trifluoroacetyl, methoxyacetyl, triphenylmethoxyacetyl, and p-chlorophenoxyacetyl), 3-phenylpropionyl, 4-oxopentanoyl, 4,4-(ethylenedithio)pentanoyl, pivaloyl (Piv), vinylpivaloyl, crotonoyl, 4-methoxy-crotonoyl, naphthoyl (e.g., 1- or 2-naphthoyl), and benzoyl (e.g., unsubstituted or substituted, e.g., p-methoxybenzoyl, phthaloyl (including salts, such a triethylamine and potassium), p-bromobenzoyl, and 2,4,6-trimethylbenzoyl). As defined herein, any heteroaryl group present in an ester group has from 1 to 4 heteroatoms selected independently from O, N, and S.

In exemplary carbonate hydroxyl protecting groups, R is C1-C12 alkyl (e.g., C1-C8, C1-C6, C1-C4, C2-C7, C3-C12, and C3-C6 alkyl), C2-C12 alkenyl (e.g., C2-C8, C2-C6, C2-C4, C3-C12, and C3-C6 alkenyl), carbocyclic C6-C20 aryl (e.g., C6-C15, C6-C10, C8-C20, and C8-C15 aryl), monocyclic C1-C6 heteroaryl (e.g., C1-C4 and C2-C6 heteroaryl), C4-C19 heteroaryl (e.g., C4-C10 heteroaryl), (C6-C15)aryl(C1-C6)alkyl, (C4-C19)heteroaryl(C1-C6)alkyl, or (C1-C6)heteroaryl(C1-C6)alkyl. Specific examples include methyl, 9-fluorenylmethyl, ethyl, 2,2,2-trichloroethyl, 2-(trimethylsilyl)ethyl, 2-(phenylsulfonyl)ethyl, vinyl, allyl, t-butyl, p-nitrobenzyl, and benzyl carbonates. As defined herein, any heteroaryl group present in a carbonate group has from 1 to 4 heteroatoms selected independently from O, N, and S.

In exemplary carbamate hydroxyl protecting groups, each R is independently H, C1-C12 alkyl (e.g., C1-C8, C1-C6, C1-C4, C2-C7, C3-C12, and C3-C6 alkyl), C2-C12 alkenyl (e.g., C2-C8, C2-C6, C2-C4, C3-C12, and C3-C6 alkenyl), carbocyclic C6-C20 aryl (e.g., C6-C15, C6-C10, C8-C20, and C8-C15 aryl), monocyclic C1-C6 heteroaryl (e.g., C1-C4 and C2-C6 heteroaryl), C4-C19 heteroaryl (e.g., C4-C10 heteroaryl), (C6-C15)aryl(C1-C6)alkyl, (C4-C19)heteroaryl(C1-C6)alkyl, or (C1-C6)heteroaryl(C1-C6)alkyl. Specific examples include N-phenyl and N-methyl-N-(o-nitrophenyl) carbamates. As defined herein, any heteroaryl group present in a carbamate group has from 1 to 4 heteroatoms selected independently from O, N, and S.

Exemplary ether hydroxyl protecting groups include C1-C12 alkylethers (e.g., C1-C8, C1-C6, C1-C4, C2-C7, C3-C12, and C3-C6 alkyl), C2-C12 alkenylethers (e.g., C2-C8, C2-C6, C2-C4, C3-C12, and C3-C6 alkenyl), (C6-C15)aryl(C1-C6)alkylethers, (C4-C19)heteroaryl(C1-C6) alkylethers, (C1-C6)heteroaryl(C1-C6)alkylethers, (C1-C6) alkoxy(C1-C6)alkylethers, (C1-C6)alkylthio(C1-C6) alkylethers, (C6-C10)aryl(C1-C6)alkoxy(C1-C6) alkylethers, and silylethers (e.g., tri(C1-C6 alkyl)silyl, tri(C6-C10 aryl or C1-C6 heteroaryl)silyl, di(C6-C10 aryl or C1-C6 heteroaryl)(C1-C6 alkyl)silyl, and (C6-C10 aryl or C1-C6 heteroaryl)di(C1-C6 alkyl)silyl). Specific examples of alkylethers include methyl and t-butyl, and an example of an alkenyl ether is allyl. Examples of alkoxyalkylethers and alkylthioalkylethers include methoxymethyl, methylthiomethyl, (2-methoxyethoxy)methyl, and β-(trimethylsilyl) ethoxymethyl. Examples of arylalkylethers include benzyl, p-methoxybenzyl (MPM), 3,4-dimethoxybenzyl, triphenylmethyl (trityl), o-nitrobenzyl, p-nitrobenzyl, p-halobenzyl, 2,6-dichlorobenzyl, p-cyanobenzyl, naphthylmethyl, and 2- and 4-picolyl ethers. Specific examples of silylethers include trimethylsilyl (TMS), triethylsilyl (TES), t-butyldimethylsilyl (TBS), t-butyldiphenylsilyl (TBDPS), triisopropylsilyl (TIPS), and triphenylsilyl (TPS) ethers. An example of an arylalkyloxyalkylether is benzyloxymethyl ether. As defined herein, any heteroaryl group present in an ether group has from 1 to 4 heteroatoms selected independently from O, N, and S.

Adjacent hydroxyl groups may be protected with a diol protecting group, such as acetal (e.g., C1-C6 alkyl), ketal (e.g., C2-C6 alkyl or C3-C6 cycloalkyl), cyclic silylene, cyclic carbonate, and cyclic boronate. Examples of acetal and ketal groups include methylene, ethylidene, benzylidene, isopropylidene, cyclohexylidene, and cyclopentylidene. An example of a cyclic silylene is di-t-butylsilylene. Another diol protecting group is 1,1,3,3-tetraisopropylsiloxanediyl. Examples of cyclic boronates include methyl, ethyl, phenyl, and 2,6-diacetamidophenyl boronates.

Protecting groups may be substituted as is known in the art; for example, aryl and arylalkyl groups, such as phenyl, benzyl, naphthyl, or pyridinyl, can be substituted with C1-C6 alkyl, C1-C6 alkoxy, nitro, cyano, carboxyl, or halogen. Alkyl groups, such as methyl, ethyl, isopropyl, n-propyl, t-butyl, n-butyl, and sec-butyl, and alkenyl groups, such as vinyl and allyl, can also be substituted with oxo, arylsulfonyl, halogen, and trialkylsilyl groups. Preferred protecting groups are TBS and Piv. Protecting groups that are orthogonal are removed under different conditions, as in known in the art.

By "leaving group" is meant a group that is displaced during a chemical reaction. Suitable leaving groups are well known in the art, e.g., see, Advanced Organic Chemistry, March, 4th Ed., pp. 351-357, John Wiley and Sons, N.Y. (1992). Such leaving groups include halogen, C1-C12 alkoxy (e.g., C1-C8, C1-C6, C1-C4, C2-C7, and C3-C6 alkoxy), C1-C12 alkylsulfonate (e.g., C1-C8, C1-C6, C1-C4, C2-C7, C3-C12, and C3-C6 alkylsulfonate), C2-C12 alkenylsulfonate (e.g., C2-C8, C2-C6, C2-C4, C3-C12, and C3-C6 alkenylsulfonate), carbocyclic C6-C20 arylsulfonate (e.g., C6-C15, C6-C10, C8-C20, and C8-C15 arylsulfonate), C4-C19 heteroarylsulfonate (e.g., C4-C10 heteroarylsulfonate), monocyclic C1-C6 heteroarylsulfonate (e.g., C1-C4 and C2-C6 heteroarylsulfonate), (C6-C15)aryl(C1-C6)alkylsulfonate, (C4-C19)heteroaryl(C1-C6)alkylsulfonate, (C1-C6)heteroaryl(C1-C6)alkylsulfonate, and diazonium. Alkylsulfonates, alkenylsulfonates, arylsulfonates, heteroarylsulfonates, arylalkylsulfonates, and heteroarylalkylsulfonates can be optionally substituted with halogen (e.g., chloro, iodo, bromo, or fluoro), alkoxy (e.g., C1-C6 alkoxy), aryloxy (e.g., C6-C15 aryloxy, C4-C19 heteroaryloxy, and C1-C6 heteroaryloxy), oxo, alkylthio (e.g., C1-C6 alkylthio), alkylenedithio (e.g., C1-C6 alkylenedithio), alkylamino (e.g., C1-C6 alkylamino), [alkenyl]alkylamino (e.g., [(C2-C6)alkenyl](C1-C6)alkylamino), [aryl]alkylamino (e.g., [(C6-C10)aryl](C1-C6)alkylamino, [(C1-C6)heteroaryl](C1-C6)alkylamino, and [(C4-C19)heteroaryl](C1-C6)alkylamino), [arylalkyl]alkylamino (e.g., [(C6-C10)aryl (C1-C6)alkyl](C1-C6)alkylamino, [(C1-C6)heteroaryl(C1-C6)alkyl](C1-C6)alkylamino, and [(C4-C19)heteroaryl(C1-C6)alkyl](C1-C6)alkylamino), dialkylamino (e.g., di(C1-C6 alkyl)amino), silyl (e.g., tri(C1-C6 alkyl)silyl, tri(C6-C10 aryl or C1-C6 heteroaryl)silyl, di(C6-C10 aryl or C1-C6 heteroaryl)(C1-C6 alkyl)silyl, and (C6-C10 aryl or C1-C6 heteroaryl)di(C1-C6 alkyl)silyl), cyano, nitro, or azido. Alkenylsulfonates can be optionally substituted with carbocyclic aryl (e.g., C6-C15 aryl), monocyclic C1-C6 heteroaryl, or C4-C19 heteroaryl (e.g., C4-C10 heteroaryl). Arylsulfonates can be optionally substituted with alkyl (e.g., C1-C6 alkyl) or alkenyl (e.g. C2-C6 alkenyl). As defined herein, any heteroaryl group present in a leaving group has from 1 to 4 heteroatoms selected independently from O, N, and S.

Specific examples of suitable leaving groups include chloro, iodo, bromo, fluoro, methanesulfonate (mesylate), 4-toluenesulfonate (tosylate), trifluoromethanesulfonate (triflate, OTf), nitro-phenylsulfonate (nosylate), and bromo-phenylsulfonate (brosylate). Leaving groups may also be further substituted as is known in the art.

By "pharmaceutically acceptable salt" is meant a salt within the scope of sound medical judgment, suitable for use in contact with the tissues of humans and animals without undue toxicity, irritation, allergic response and the like and commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethane sulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts and the like. A preferred salt is the mesylate salt.

Other features and advantages of the invention will be apparent from the following description and the claims.

DETAILED DESCRIPTION OF THE INVENTION

The present invention provides compounds and methods of their use in the synthesis of halichondrin B analogs. In particular, the compounds are useful for the synthesis of the C14-C35 portion of halichondrin B analogs. ER-804028 is a C14-C35 fragment that has been employed in the synthesis of eribulin:

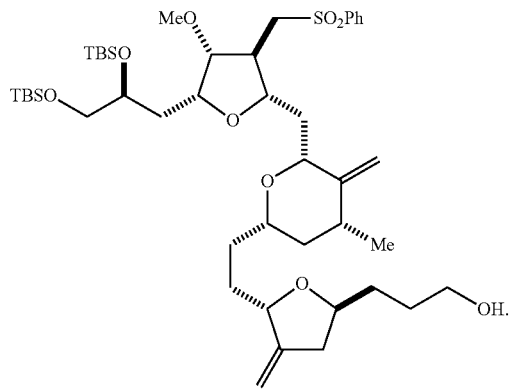

ER-804028

Halichondrin B analogs, e.g., eribulin or pharmaceutically acceptable salts thereof, can be synthesized from the C14-C35 fragment as described in U.S. Pat. No. 6,214,865 and International Publication No. WO 2005/118565. In one example described in these references, the C14-C35 portion, e.g., ER-804028, of the molecule is coupled to the C1-C13 portion, e.g., ER-803896, to produce ER-804029, and additional reactions are carried out to produce eribulin (Scheme 1):

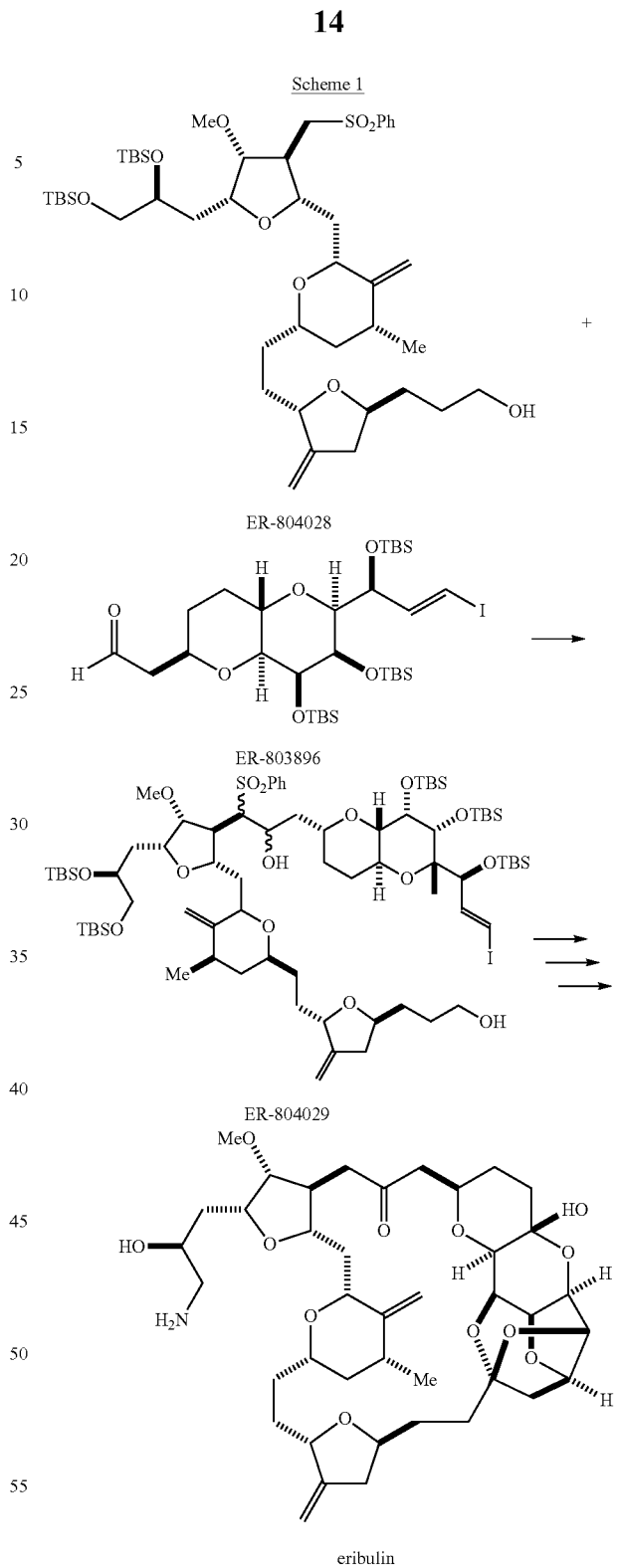

Lithiation of the C14-C35 sulfone fragment followed by coupling to the C1-C13 aldehyde fragment furnishes a mixture of diastereomeric alcohols (ER-804029). Additional protecting group manipulation and oxidation followed by removal of the sulfonyl group and an intramolecular Nozaki-Hiyama-Kishi (NHK) reaction affords an intermediate, which, when oxidized and treated with tetrabutylammonium fluoride, undergoes intramolecular oxy-Michael ring closure.

Pyridinium p-toluenesulfonate mediated ketal formation and conversion of the terminal alcohol to an amine furnishes eribulin.

For example, as described in WO 2005/118565 (Example 6), ER-804029 is reacted to produce ER-804030; ER-804030 is reacted to produce ER-118049; ER-118049 is reacted to produce mixture ER-118047/118048; the mixture ER-118047/118048 is reacted to produce ER-118046; ER-118046 is reacted to produce ER-811475; ER-811475 is reacted to produce ER-076349; and ER-076349 is reacted to produce eribulin.

Pharmaceutically acceptable salts of eribulin, e.g., eribulin mesylate, can be formed by methods known in the art, e.g., in situ during the final isolation and purification of the compound or separately by reacting the free base group with a suitable organic acid. In one example, eribulin is treated with a solution of MsOH and $NH_4OH$ in water and acetonitrile. The mixture is concentrated. The residue is dissolved in DCM-pentane, and the solution is added to anhydrous pentane. The resulting precipitate is filtered and dried under high vacuum to provide eribulin mesylate, as shown in Scheme 2.

Scheme 2

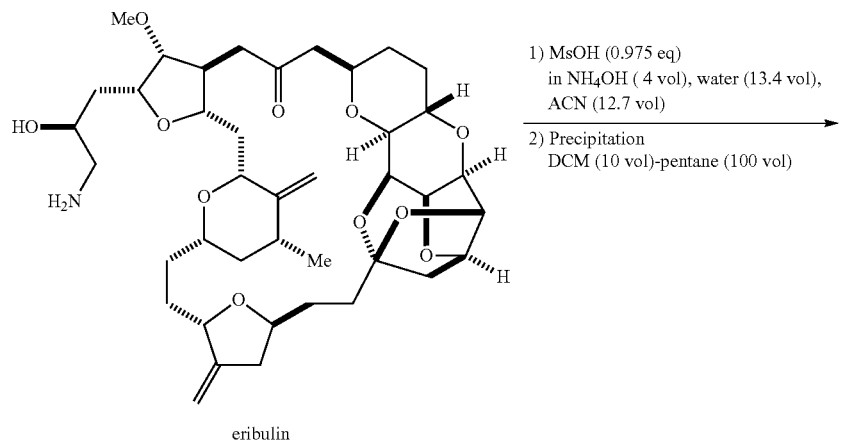

eribulin

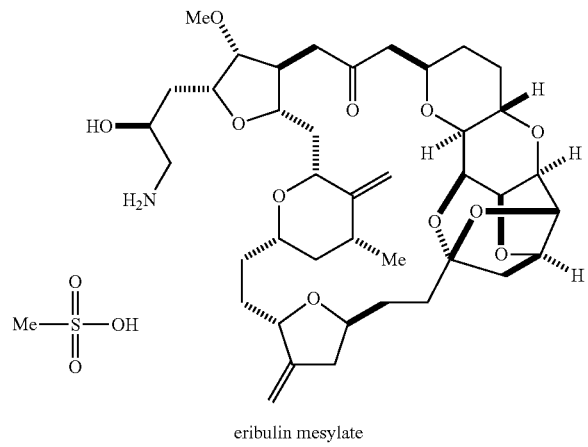

eribulin mesylate

A scheme for producing one example of a C14-C35 fragment (ER-804028) is as follows (Scheme 3).

Scheme 3

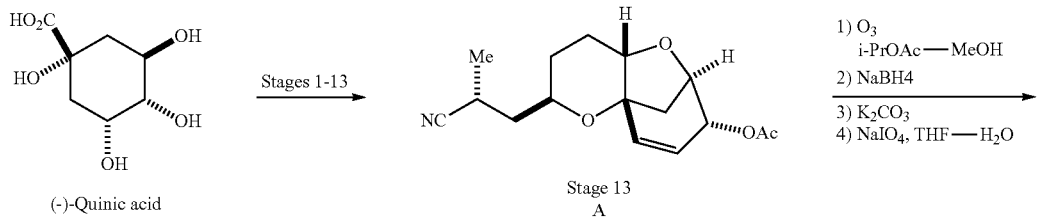

(-)-Quinic acid

Stage 13
A

-continued
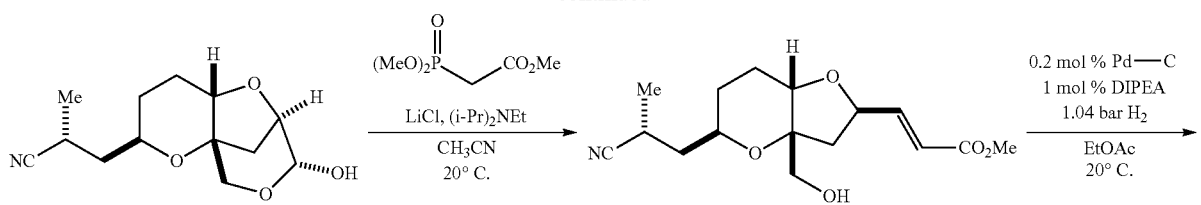
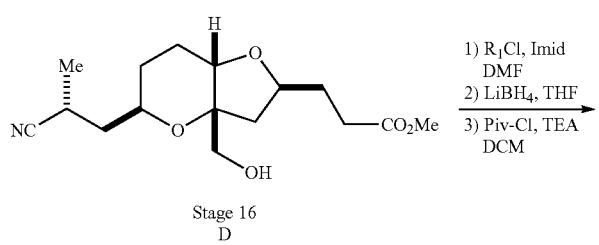
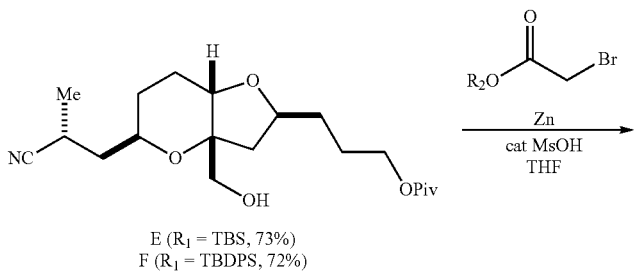
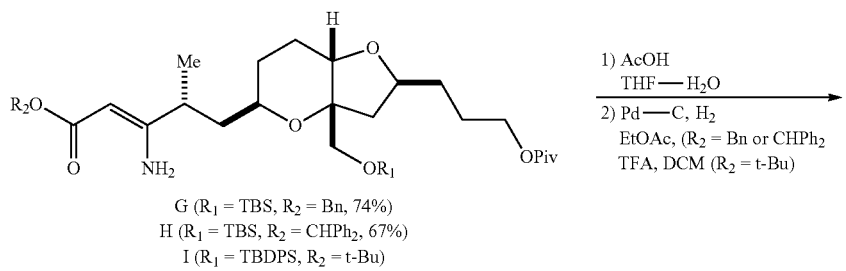
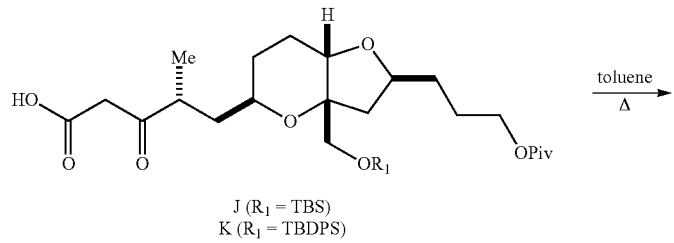
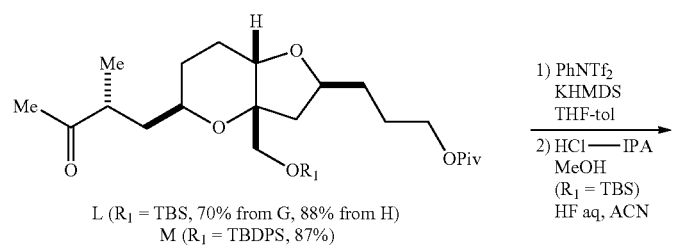

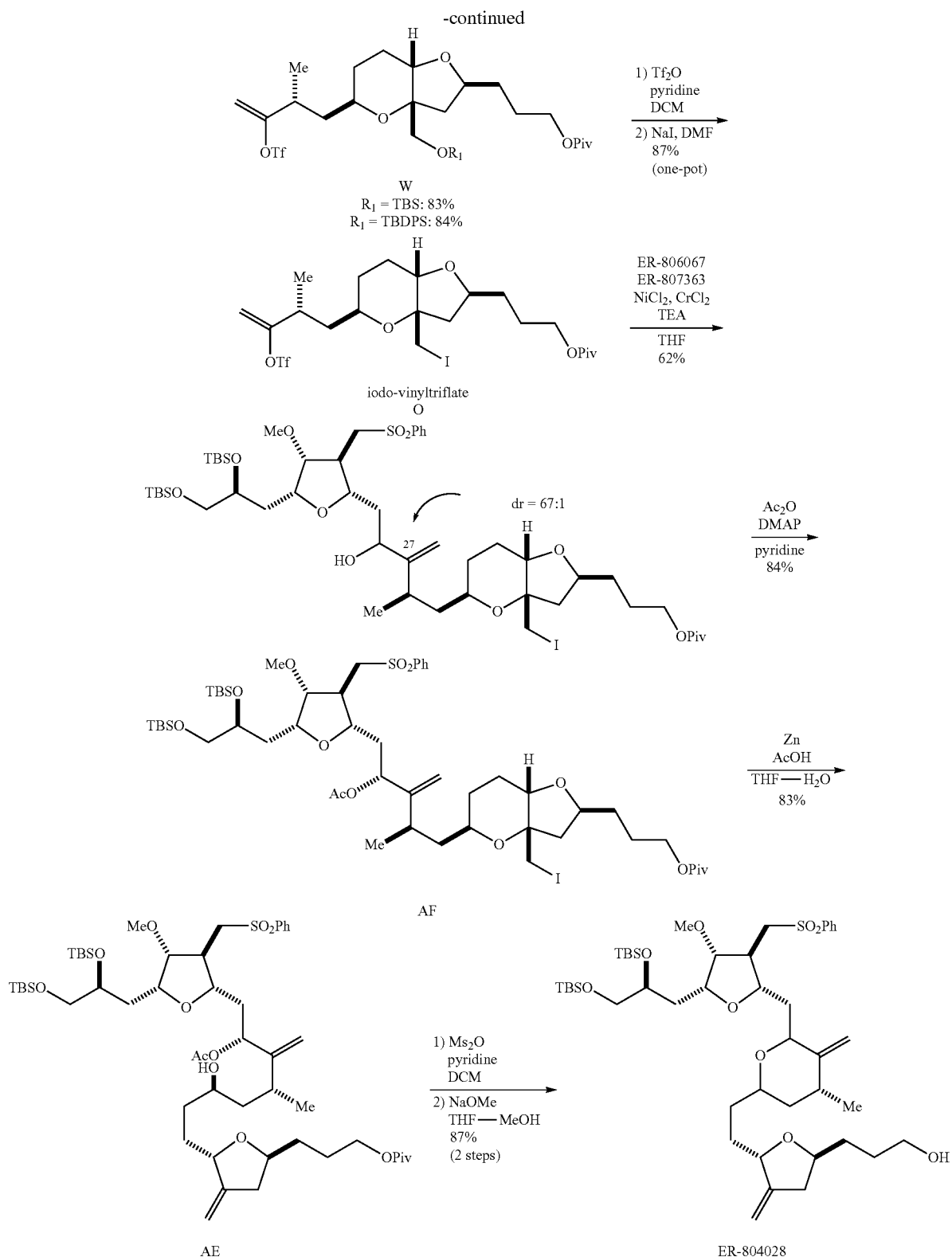

Generally, (−)-quinic acid is converted to Compound A through stages 1-13 as described in International Publication Nos. WO 2009/046308 and WO 2005/118565. As outlined in Scheme 3, oxidation followed by Horner-Wadsworth-Emmons (HWE) reaction of the resulting lactol, hydrogenation, and protecting group modification furnishes Compounds E and F. Blaise reaction followed by methyl ketone formation, dehydration, enolization, triflation, desilylation, and iodination produces iodo-vinyl triflate, Compound O. NHK coupling of Compound O with ER-806067 furnishes Compound P. Acetylation followed by Vasella fragmentation, intramolecular Williamson etherification, and protecting group modification affords C14-C35 fragment ER-804028. This scheme is advantageous as it results in improved stereoselectivity at C27, i.e., 67:1 dr compared to 13:1 dr in previous processes. The scheme is also advantageous as the C14-C26 starting material and C14-C35 product of the NHK coupling of this scheme exhibit greater stability than the starting material and product of previous methods. The C14-C26 starting material and C14-C35 product of the NHK coupling are stable indefinitely at room temperature, allowing for a flexible manufacturing schedule.

One skilled in the art would also understand that variations on the above scheme are possible. For example, the hydroxyl protecting groups employed in particular reactions may be varied. In other variations, the leaving groups employed may be altered; for example, triflate groups can be replaced with halogens such as iodine or bromine.

In addition, although the scheme depicts Compound C et seq. with carbons C14-C16, the reactions leading to the addition of carbons C14 and C15 can occur at any point prior to the synthesis of ER-804028. Synthetic steps for adding carbons C14 and C15 are disclosed in WO 2009/046308. In specific examples, Compound A or Compound B can be altered as shown in Scheme 4, and the products AG and AH substituted for Compound E or F in Scheme 3.

Scheme 4

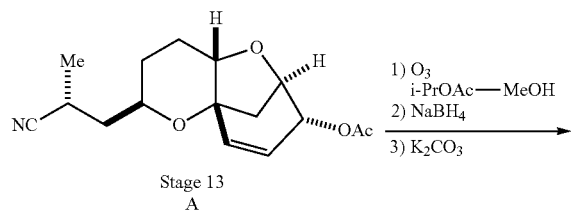

Stage 13
A

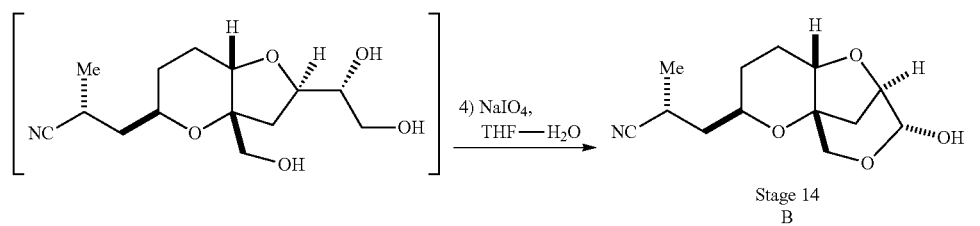

Stage 14
B

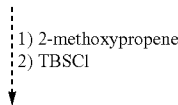
1) 2-methoxypropene
2) TBSCl

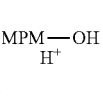
MPM—OH
H+

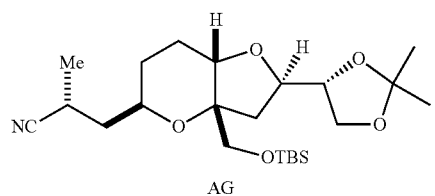

AG

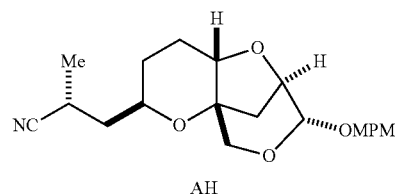

AH

In accordance with the synthetic scheme, the invention provides compounds having the formula:

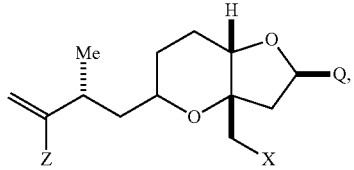
(I)

e.g., Compound O, Compound AI, and Compound AJ, wherein X is halogen or oxo; Z is a leaving group; Q is —C(O)H, —CH═CHC(O)OY$_1$, —C(R)H(CH$_2$)$_n$OY$_1$, or —C(R)HCH$_2$C(O)OY$_1$; R is H or —OY$_2$; Y$_1$ and Y$_2$ are each independently H or a hydroxyl protecting group; and n is 1 or 2. When both Y$_1$ and Y$_2$ are present, they may be the same or different. In addition, when Y$_1$ and Y$_2$ are on adjacent carbons, e.g., when n=1, they may together form a divalent hydroxyl protecting group. Compounds of this formula include those having the formula:

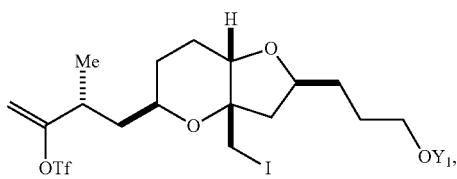
(Ib)

wherein Y$_1$ is H, pivaloyl, benzoyl, p-bromobenzoyl, 1-naphthoyl, 2-naphthoyl, p-methoxybenzoyl, or o-phthaloyl (including salts such as triethylamine and potassium).

The invention also provides compounds having the formula:

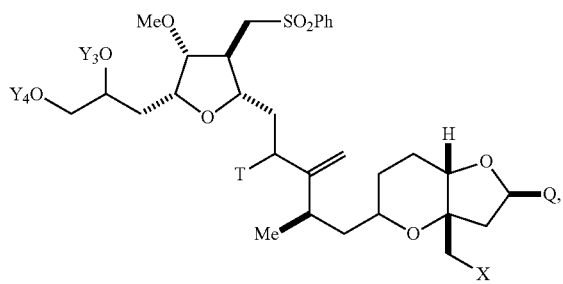
(II)

e.g., Compound P, Compound AD, Compound AF, Compound AK, Compound AL, and Compound AM, wherein X is halogen or oxo; Q is —C(O)H, —CH═CHC(O)OY$_1$, —C(R)H(CH$_2$)$_n$OY$_1$, or —C(R)HCH$_2$C(O)OY$_1$; R is H or —OY$_2$; n is 1 or 2; Y$_1$, Y$_2$, Y$_3$, and Y$_4$ are each independently H or a hydroxyl protecting group; T is oxo or —OY$_5$; and Y$_5$ is H or a hydroxyl protecting group, or Y$_5$, together with the oxygen atom to which it is bound, is a leaving group. In certain embodiments, Y$_3$ and Y$_4$ are together a divalent hydroxyl protecting group. In other embodiments, Y$_1$, Y$_3$, and Y$_4$ are protecting groups, and Y$_1$ is orthogonal to Y$_3$ and Y$_4$. In further embodiments, Y$_1$, Y$_3$, Y$_4$, and Y$_5$ are protecting groups; Y$_3$ and Y$_4$ are orthogonal to Y$_1$ and Y$_5$; and Y$_1$ is orthogonal to Y$_5$. Compounds of this formula include those having the formula:

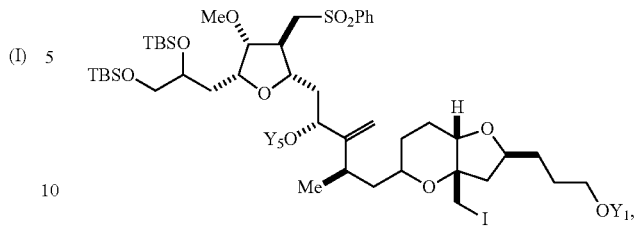
(IIc)

wherein Y$_1$ and Y$_5$ are as follows:

| Y$_1$ | Y$_5$ |
|---|---|
| H | H |
| benzoyl | benzoyl |
| p-bromobenzoyl | p-bromobenzoyl |
| pivaloyl | H |
| pivaloyl | acetyl |
| pivaloyl | benzoyl |
| 2-naphthoyl | H |
| 2-naphthoyl | 2-naphthoyl |
| 1-naphthoyl | H |
| 1-naphthoyl | 1-naphthoyl |
| p-methoxybenzoyl | H |
| p-methoxybenzoyl | p-methoxybenzoyl |
| o-phthaloyl | H |
| o-phthaloyl, triethylamine salt | H |

The invention also features compounds having the formula:

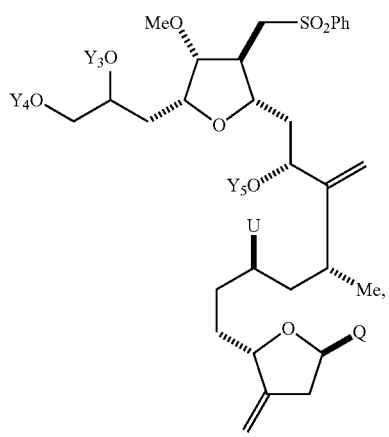
(III)

e.g., Compound AE, wherein Q is —C(O)H, —CH═CHC(O)OY$_1$, —C(R)H(CH$_2$)$_n$OY$_1$, or —C(R)HCH$_2$C(O)OY$_1$; R is H or —OY$_2$; n is 1 or 2; Y$_1$, Y$_2$, Y$_3$, and Y$_4$ are each independently H or a hydroxyl protecting group; U is halogen or —OY$_6$; Y$_5$ is H or a hydroxyl protecting group or Y$_5$, together with the oxygen atom to which it is bound, is a leaving group; and Y$_6$ is H or a hydroxyl protecting group or Y$_6$, together with the oxygen atom to which it is bound, is a leaving group, provided that when Q is —C(R)H(CH$_2$)$_n$OY$_1$ (e.g., —(CH$_2$)$_3$OY$_1$), U is —OY$_6$, —OY$_6$ is a leaving group, and Y$_1$, Y$_3$, and Y$_4$ are protecting groups, Y$_5$ is not H. In certain embodiments, Y$_3$ and Y$_4$ are together a divalent hydroxyl protecting group. In other embodiments, Y$_1$, Y$_3$, and Y$_4$ are protecting groups, and $Y_1$ is orthogonal to $Y_3$ and $Y_4$. In further embodiments, $Y_1$, $Y_3$, $Y_4$, and $Y_5$ are protecting groups; $Y_3$ and $Y_4$ are orthogonal to $Y_1$ and $Y_5$; and $Y_1$ is orthogonal to $Y_5$.

As described herein, the compounds of the invention can be used in the synthesis of ER-804028 and in turn eribulin, or a pharmaceutically acceptable salt thereof, e.g., eribulin mesylate.

EXPERIMENTAL PROCEDURES

Compound D

The synthesis of Compound D from (−)-quinic acid is described in WO 2009/046308, which is hereby incorporated by reference.

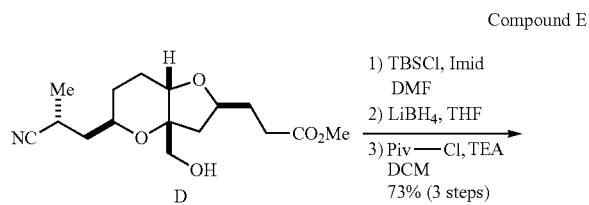

Compound D (3.05 g, 9.80 mmol, 1 eq) was dissolved in DMF (6.1 ml) at 22° C., and imidazole (1.00 g, 14.7 mmol, 1.5 eq) was added. Upon complete dissolution of imidazole, the mixture was cooled to 0° C., and TBSCl (1.55 g, 10.3 mmol, 1.05 eq) was added. The mixture was stirred at 0° C. for 1 h, allowed to warm to room temperature and stirred for an additional 1 h. The reaction mixture was diluted with MTBE (37 ml) and washed with water (30 ml). The organic layer was separated, further washed with water (9.2 ml), and concentrated to give Compound S:

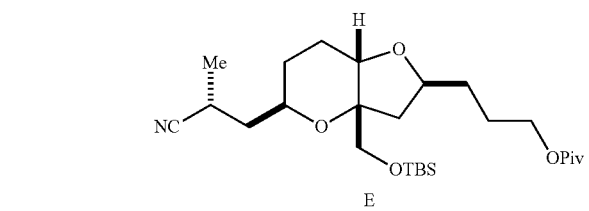

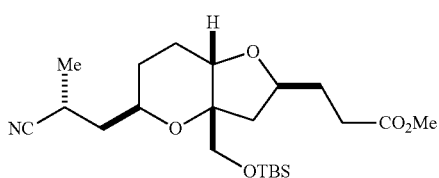

as colorless oil (4.43 g with residual solvents, theoretical 100% yield assumed). The crude product was used for the next reaction without purification. $^1$H NMR (400 MHz, CDCl$_3$): δ 4.20 (1H, m), 3.91 (1H, m), 3.85 (1H, m), 3.64 (3H, s), 3.50 (1H, d, J=10.8 Hz) 3.45 (1H, d, J=10.8 Hz), 2.90 (1H, m), 2.39 (1H, m), 2.31 (1H, m), 2.22 (1H, dd, J=14.0 Hz, 8.8 Hz), 1.77-1.90 (2H, m), 1.60-1.74 (4H, m), 1.51 (1H, m), 1.27 (3H, d, J=6.8 Hz), 1.26 (1H, m), 0.86 (9H, s), 0.02 (6H, s); and $^{13}$C NMR (100 MHz, CDCl$_3$): δ 174.08, 122.93, 84.86, 75.78, 73.45, 66.82, 66.31, 51.77, 41.04, 38.16, 31.44, 31.04, 26.20, 26.06 (3C), 22.51, 22.20, 18.51, 18.48, −5.12, −5.17.

Compound S (4.2 g, 9.8 mmol, 1 eq) was dissolved in THF (21 ml) and cooled to 0° C. LiBH$_4$ (2.0 M solution in THF, 12.2 ml, 24.5 mmol, 2.5 eq) was added, and the mixture was allowed to warm to 20° C. Stirring was continued at 20-23° C. overnight (16 h). Another reactor was charged with 20 wt % citric acid (aqueous solution, 25 g, 26 mmol, 2.6 eq) and MTBE (40 ml), and the mixture was cooled to 0° C. The reaction mixture was carefully/slowly poured into the pre-chilled citric acid-MTBE while maintaining T-internal <10° C. Upon complete addition, the mixture was stirred at 0-5° C. for 30 min. The organic layer was separated, sequentially washed with: 1) saturated NaHCO$_3$ (12 g) and 2) 20 wt % NaCl (12 g), and concentrated to give crude Compound T:

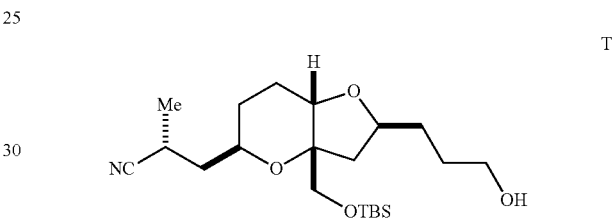

as colorless oil (3.32 g, 8.3 mmol, 85% yield in 2 steps). $^1$H NMR (400 MHz, CDCl$_3$): δ 4.20 (1H, m), 3.93 (1H, dd, J=6.4 Hz, 4.8 Hz), 3.80 (1H, m), 3.57 (2H, m), 3.47 (1H, d, J=10.4 Hz), 3.42 (1H, d, J=10.4 Hz), 2.88 (1H, m), 2.57 (1H, br), 2.18 (1H, dd, J=7.2 Hz, 14.4 Hz), 1.68-1.81 (2H, m), 1.45-1.68 (6H, m), 1.24 (3H, d, J=7.2 Hz), 1.22 (1H, m), 0.83 (9H, s), 0.02 (6H, s); and $^{13}$C NMR (100 MHz, CDCl$_3$): δ 122.90, 84.72, 76.75, 73.56, 67.14, 66.53, 62.87, 40.94, 38.18, 33.58, 29.91, 26.36, 26.04, 22.60, 22.48 (3C), 18.478, 18.43, −5.11, −5.16.

Compound T (2.30 g, 5.78 mmol, 1 eq) was dissolved in CH$_2$Cl$_2$ (12 ml). TEA (1.6 ml, 12 mmol, 2.0 eq) was added followed by DMAP (71 mg, 0.58 mmol, 0.10 eq). The mixture was cooled to 0° C., and pivaloyl chloride (0.747 ml, 6.07 mmol, 1.05 eq) was added. The mixture was allowed to warm to 0° C., and stirring was continued at 20-22° C. for an additional 2 h. The reaction mixture was diluted with MTBE (23 ml), sequentially washed with: 1) 20 wt % citric acid (aqueous solution, 12 g, 12 mmol, 2.1 eq) and 2) saturated NaHCO$_3$ (aqueous solution, 4.6 g, 5.5 mmol, 0.95 eq), and concentrated to give crude product as pale yellow oil. The crude was purified by Biotage (Uppsala, Sweden) 40M (heptane-MTBE 7:3 v/v) to give Compound E as pale yellow oil (2.79 g, 5.04 mmol, 87% yield). $^1$H NMR (400 MHz, CDCl$_3$): δ 4.22 (1H, m), 4.04 (1H, d, J=6.4 Hz), 4.03 (1H, d, J=6.4 Hz), 4.93 (1H, dd, J=3.2 Hz, 6.4 Hz), 3.85 (1H, m), 3.50 (1H, d, J=10.4 Hz), 3.45 (1H, d, J=10.4 Hz), 2.92 (1H, m), 2.21 (1H, dd, J=8.4 Hz, 13.6 Hz), 1.48-1.85 (7H, m), 1.43 (1H, m), 1.29 (3H, d, J=7.6 Hz), 1.25 (1H, m), 1.17 (9H, s), 0.87 (9H, s), 0.02 (6H, s); and $^{13}$C NMR (100 MHz, CDCl$_3$): δ 178.78, 122.96, 84.83, 76.25, 73.45, 67.11, 66.53, 64.43, 41.00, 38.94, 37.89, 32.98, 27.42 (3C), 26.47, 26.06 (3C), 25.60, 22.60, 22.52, 18.51, 18.48, −5.09, −5.15.

Compound G

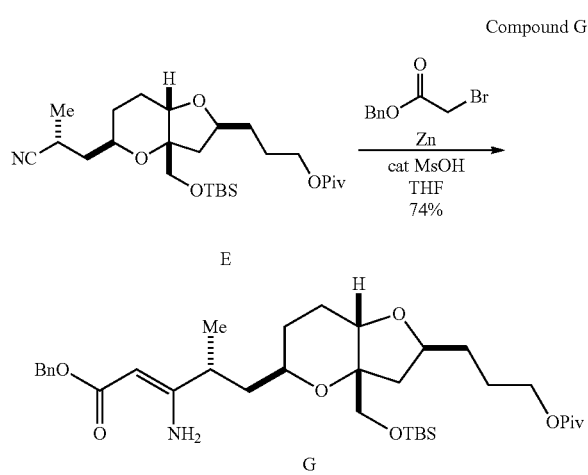

Zinc dust (876 mg, 13.4 mmol, 10.0 eq) was suspended in THF (3.9 ml). MsOH (0.0087 ml, 0.13 mmol, 0.10 eq) was added, and the mixture was heated at reflux for 20 min. A mixture of Compound E (0.645 g, 1.34 mmol, 1 eq) and benzyl bromoacetate (0.315 ml, 2.01 mmol, 1.50 eq) in THF (2.6 ml+1.3 ml) was added under reflux. After 2 h, benzyl bromoacetate (0.10 ml, 0.67 mmol, 0.50 eq) was added, and heating was continued for an additional 3 h (total 5 h). After cooling down, the reaction mixture was diluted with MTBE (10 ml) and cooled to 5° C. 20 wt % citric acid (aqueous solution, 3.2 g, 3.4 mmol, 2.5 eq) was added, and vigorous stirring was continued at 5-10° C. for 10 min. The whole mixture was filtered through a pad of Celite (1.3 g). The organic layer was separated and set aside. The aqueous layer was extracted with MTBE (10 ml). All organic layers were combined, sequentially washed with: 1) saturated NaHCO$_3$ (aqueous solution, 3.2 g) and 2) 20 wt % NaCl (aqueous solution, 3.2 g), and concentrated to give crude product as yellow oil. The crude was purified by Biotage (Uppsala, Sweden) 25M (heptane-MTBE 3:1 & 3:2 v/v) to give Compound G as pale yellow oil (0.627 g, 0.992 mmol, 74% yield). $^1$H NMR (400 MHz, CDCl$_3$): δ 7.95 (1H, br), 7.24-7.37 (5H, m), 5.11 (1H, d, J=12.8 Hz), 5.07 (1H, d, J=12.8 Hz), 4.58 (1H, s), 4.10 (1H, m), 4.02 (2H, m), 3.78 (1H, dd, J=5.6 Hz, 7.2 Hz), 3.56 (1H, m), 3.54 (1H, d, J=10.4 Hz), 3.46 (1H, d, J=10.4 Hz), 2.46 (1H, m), 2.15 (1H, dd, J=8.8 Hz, 14.0 Hz), 1.35-1.82 (10H, m), 1.18 (1H, m), 1.17 (9H, s), 1.10 (3H, d, J=6.8 Hz), 0.88 (9H, s), 0.04 (6H, s); and $^{13}$C NMR (100 MHz, CDCl$_3$): δ 178.77, 170.63, 168.91, 137.49, 128.66 (2C), 127.99 (2C), 127.19, 84.27, 81.26, 75.91, 73.63, 67.52, 67.17, 64.71, 64.44, 42.75, 38.94, 37.03, 35.46, 33.22, 27.43 (3C), 26.08, 26.01 (3C), 25.56, 23.50, 20.06, 18.51, −5.09 (2C).

Compound L

Compound G (0.596 g, 0.943 mmol, 1 eq) was dissolved in THF (3.0 ml)-water (1.0 ml) and cooled to 10° C. AcOH (2.0 ml, 35 mmol, 37 eq) was added, and the mixture was allowed to warm to room temperature. After 10 h, the reaction mixture was poured into a pre-chilled (0° C.) mixture of NaHCO$_3$ (4.8 g, 57 mmol, 60 eq), water (6 ml), and MTBE (20 ml). The organic layer was separated, washed with water (6 ml), and concentrated to give crude product. The crude was azeotroped with toluene (20 ml) and purified by Biotage (Uppsala, Sweden) 25 M (heptane-EtOAc 9:1 v/v) to give Compound U:

(0.493 g, 0.779 mmol, 82% yield) as colorless oil.

An inert flask was charged with 10 wt % Pd—C (wet-type, 15 mg, 0.014 mmol, 0.050 eq). A solution of Compound U (0.182 g, 0.288 mmol, 1 eq) in EtOAc (3.6 ml) was added under N$_2$. The internal atmosphere was replaced with H$_2$, and stirring was continued at room temperature for 2 h. The mixture was filtered through a pad of Celite (1.0 g). The reactor and the filter cake were rinsed with EtOAc (3.6 ml). The filtrate was concentrated to give crude keto-acid Compound J as colorless film. A portion (10%) of crude Compound J was retained for analytical and stability testing. The remaining portion (90%) of Compound J was dissolved in toluene (3.0 ml). The mixture was heated at 95° C. for 15 min and then concentrated to give crude product as pale yellow oil. The crude was purified by Biotage (Uppsala, Sweden) 12M (heptane-EtOAc 95:5 v/v) to give Compound L (110 mg, 0.220 mmol, 85% adjusted yield) as colorless oil. $^1$H NMR (400 MHz, CDCl$_3$): δ 4.08 (1H, m), 4.00 (1H, d, J=6.8 Hz), 3.98 (1H, d, J=6.8 Hz), 3.81 (1H, t, J=5.6 Hz), 3.49 (1H, m), 3.44 (1H, d, J=10.4 Hz), 3.39 (1H, d, J=10.4 Hz), 2.73 (1H, m), 2.09 (3H, s), 1.99 (1H, dd, J=8.8 Hz, 14.0 Hz), 1.32-1.75 (10H, m), 1.16 (1H, m), 1.13 (9H, s), 1.03 (3H, d, J=7.2 Hz), 0.84 (9H, s), 0.07 (6H, s); and $^{13}$C NMR (100 MHz, CDCl$_3$): δ 212.79, 178.68, 84.49, 76.05, 73.52, 67.30, 66.67, 64.38, 43.45, 39.79, 39, 37.22, 32.98, 28.75, 27.37 (3C), 26.91, 26.04 (3C), 25.53, 22.85, 18.47, 17.26, −5.15, −5.20.

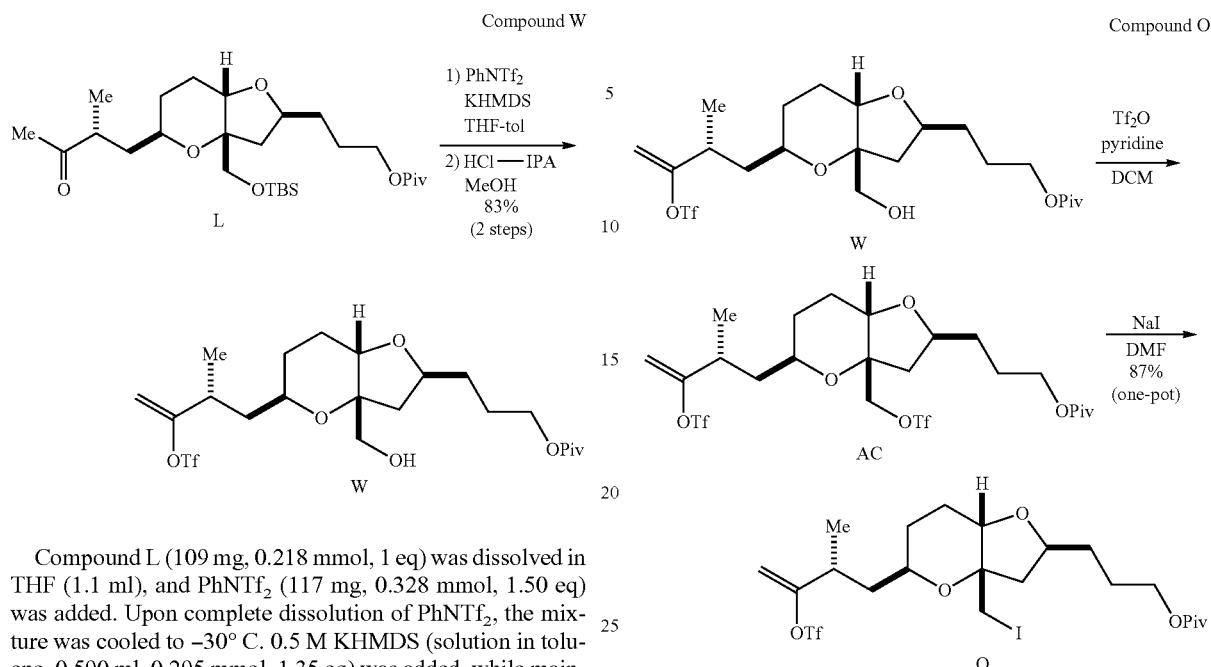

Compound L (109 mg, 0.218 mmol, 1 eq) was dissolved in THF (1.1 ml), and PhNTf₂ (117 mg, 0.328 mmol, 1.50 eq) was added. Upon complete dissolution of PhNTf₂, the mixture was cooled to −30° C. 0.5 M KHMDS (solution in toluene, 0.590 ml, 0.295 mmol, 1.35 eq) was added, while maintaining T-internal <−25° C. Upon complete addition, stirring was continued at −25° C. for 1 h. 20 wt % NH₄Cl (aqueous solution, 0.33 g, 1.2 mmol, 5.6 eq) was added while maintaining T-internal <−20° C., and the resultant mixture was allowed to warm to 0° C. The mixture was diluted with water (0.33 g) and MTBE (2.2 ml) and then further stirred for 5 min. The organic layer was separated, washed with saturated NaHCO₃ (aqueous solution, 0.54 g), and concentrated to give crude Compound V:

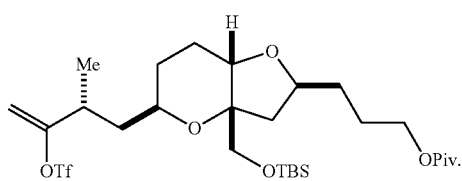

Compound V was dissolved in MeOH (1.0 ml) and treated with 6 M HCl (solution in 2-propanol, 0.25 ml, 2 mmol, 7 eq) at 20° C. After 1 h, the reaction mixture was cooled to 0° C., neutralized with saturated NaHCO₃ (1.6 g) and extracted with MTBE (6 ml). The organic layer was separated, washed with 20 wt % NaCl (0.54 g), and concentrated to give crude product as pale yellow oil. The crude was purified by Biotage (Uppsala, Sweden) 12M (heptane-MTBE 1:1 & 3:7 v/v) to give Compound W (94.1 mg, 0.182 mmol, 83% yield) as colorless oil. $^1$H NMR (400 MHz, CDCl₃): δ 5.09 (1H, d, J=3.6 Hz), 4.87 (1H, d, J=3.6 Hz), 4.12 (1H, m), 4.03 (1H, m), 3.84 (1H, dd, J=6.4 Hz, 8.8 Hz), 3.59 (1H, m), 3.49 (1H, d, J=11.2 Hz), 3.45 (1H, d, J=11.2 Hz), 2.68 (1H, m), 2.19 (1H, dd, J=8.8 Hz, 14.0 Hz), 2.13 (1H, br), 1.87 (1H, m), 1.40-1.75 (8H, m), 1.35 (1H, dd, J=5.6 Hz, 14.0 Hz), 1.20 (1H, m), 1.16 (9H, s), 1.13 (3H, d, J=6.8 Hz); and $^{13}$C NMR (100 MHz, CDCl₃): δ 178.75, 160.06, 120.20, 103.03, 83.76, 75.16, 73.41, 68.59, 67.83, 64.25, 40.08, 38.94, 35.47, 35.21, 33.36, 28.05, 27.39 (3C), 25.51, 24.55, 18.90.

Compound W (90.0 mg, 0.174 mmol, 1 eq) was dissolved in CH₂Cl₂ and cooled to −10° C. Pyridine (0.042 ml, 0.52 mmol, 3.0 eq) was added, followed by Tf₂O (0.044 ml, 0.26 mmol, 1.5 eq) (T-internal <−3° C.). After stirring at −5 to 0° C. for 1 h, DMF (0.45 ml) was added, followed by NaI (78 mg, 0.52 mmol, 3.0 eq). Stirring was continued at 20-22° C. for 3 h, and then the reaction mixture was poured into a pre-chilled (0° C.) mixture of MTBE (2.0 ml) and water (2.0 ml). The organic layer was separated and set aside. The aqueous layer was extracted with MTBE (2.0 ml). All organic layers were combined, washed with a mixture of water (0.4 ml) and 10 wt % Na₂SO₃ (0.9 g), and concentrate to give crude product as yellow oil. The crude was purified by Biotage (Uppsala, Sweden) 12M (heptane-MTBE 85:15 v/v) to give Compound O (95.6 mg, 0.153 mmol, 87% yield from Compound W) as colorless oil. $^1$H NMR (400 MHz, CDCl₃): δ 5.08 (1H, d, J=3.6 Hz), 5.01 (1H, d, J=3.6 Hz), 4.18 (1H, m), 4.05 (2H, m), 3.74 (1H, dd, J=6.4 Hz, 9.2 Hz), 3.53 (1H, m), 3.44 (1H, dd, J=1.2 Hz, 10.0 Hz), 3.37 (1H, d, J=10.0 Hz), 2.84 (1H, m), 2.32 (1H, dd, J=8.8 Hz, 14.0 Hz), 1.85 (1H, m), 1.44-1.76 (9H, m), 1.22 (1H, m), 1.17 (9H, s), 1.13 (3H, d, J=6.8 Hz); and $^{13}$C NMR (100 MHz, CDCl₃): δ 178.75, 159.70, 120.20, 103.21, 81.42, 76.18, 75.51, 68.06, 64.18, 39.71, 38.96, 37.69, 35.43, 33.40, 27.94, 27.42 (3C), 25.51, 25.10, 20.10, 18.72.

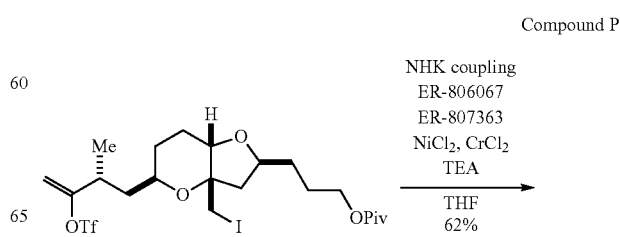

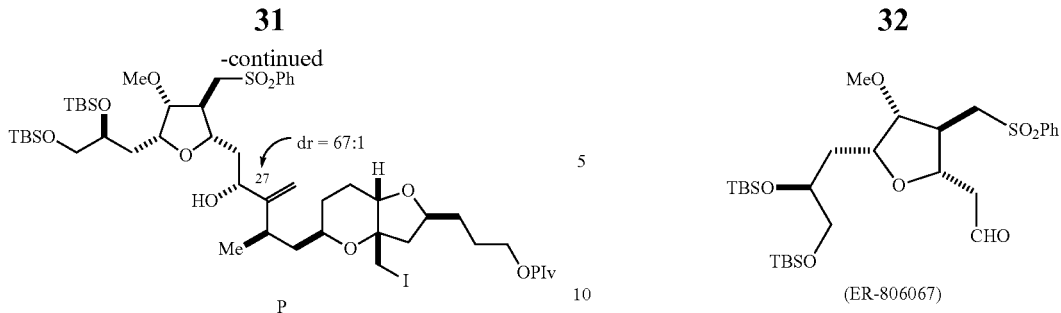

A solution of ER-807363:

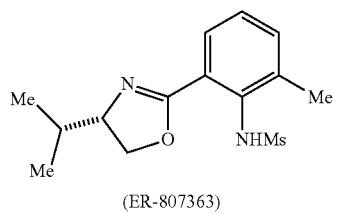

(ER-807363)

(4.10 g, 13.8 mmol, 3.55 eq; WO 2005/118565) in THF (34.2 ml) was purged with N₂ for 1 h, and CrCl₂ (1.70 g, 13.8 mmol, 3.55 eq) was added under N₂. The mixture was heated to 35° C., and TEA (1.93 ml, 13.8 mmol, 3.55 eq) was added while maintaining T-internal <38° C. The mixture was heated at 30-35° C. for 1 h and cooled to 0° C. NiCl₂ (75.7 mg, 0.15 eq) was added, and the mixture was purged with N₂ for 3 min. A previously degassed mixture of Compound O (2.44 g, 3.89 mmol, 1 eq), and ER-806067:

(2.57 g, 4.28 mmol, 1.10 eq; WO 2005/118565) in THF (17 ml) was added. The reaction was allowed to warm to 22° C. over 30 min, and stirring was continued at 22-24° C. for 20 h. The reaction mixture was cooled to 0° C. and diluted with heptane (70 ml). A solution of ethylenediamine (2.1 ml, 31 mmol, 8.0 eq) in water (12 ml) was added while maintaining T-internal <5° C. The resultant mixture was vigorously stirred at 0° C. for 1 h and filtered through a pad of Celite (2.4 g, rinsed with 12 ml heptane). The organic layer was separated, washed with water (12 ml), and concentrated to give a green solid-oil, which was suspended in heptane (20 ml), filtered for removal of ER-807363, and re-concentrated to give crude product. The crude was purified by Biotage (Uppsala, Sweden) 25M (heptane-MTBE 2:1 & 1:1) to give Compound P (2.64 g, 2.44 mmol, 62% yield; C27-dr 67:1) as pale yellow oil. $^{1}$H NMR (400 MHz, CDCl₃): δ 7.88 (2H, m), 7.64 (1H, m), 7.57 (2H, m), 5.17 (1H, s), 4.84 (1H, s), 4.12 (2H, m), 4.00 (2H, m), 3.91 (1H, m), 3.72 (4H, m), 3.53 (1H, dd, J=5.6 Hz, 10.0 Hz), 3.30-3.50 (4H, m), 3.35 (3H, s), 3.06 (2H, m), 2.55 (1H, m), 2.34 (1H, dd, J=8.8 Hz, 13.6 Hz), 2.28 (1H, m), 1.97 (1H, m), 1.88 (1H, m), 1.40-1.83 (13H, m), 1.14 (9H, s), 1.03 (3H, d, J=6.8 Hz), 0.85 (18H, s), 0.05 (6H, s), 0.01 (6H, s); and $^{13}$C NMR (100 MHz, CDCl₃): δ 178.71, 156.78, 139.72, 134.26, 129.74 (2C), 128.06 (2C), 107.98, 85.78, 83.71, 81.19, 79.09, 76.36, 75.43, 73.77, 71.33, 68.86, 67.95, 64.22, 58.35, 57.65, 44.46, 44.31, 41.51, 38.92, 37.39, 33.60, 33.40, 32.31, 28.30, 27.43, 27.19, 26.20 (6C), 26.15 (3C), 25.50, 25.20, 22.65, 20.84, 18.58, 18.37, −3.89, −4.49, −5.10 (2C).

Compound AF

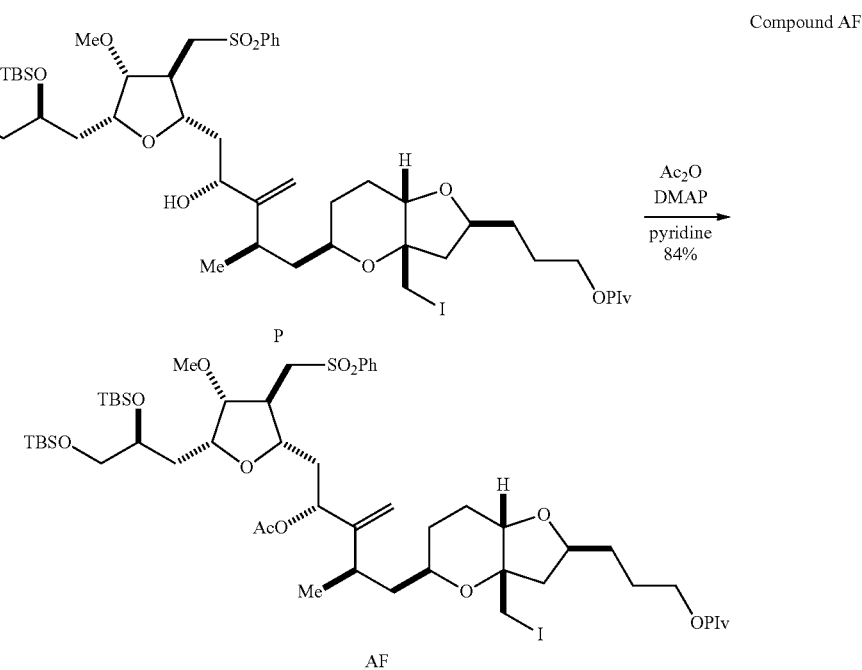

Compound P (620 mg, 0.574 mmol, 1 eq) was dissolved in pyridine (1.2 ml, 15 mmol, 27 eq). $Ac_2O$ (0.31 ml, 3.3 mmol, 5.7 eq) was added, followed by DMAP (7.0 mg, 0.057 mmol, 0.10 eq). After stirring at 20-23° C. for 3 h, the reaction mixture was diluted with toluene (12 ml) and concentrated. The same operation was repeated with toluene (12 ml×2) to give crude product. The crude was purified by Biotage (Uppsala, Sweden) 25M (heptane-MTBE 7:3 v/v) to give Compound AF (541 mg, 0.482 mmol, 84% yield) as colorless oil. $^1H$ NMR (400 MHz, $CDCl_3$): δ 7.93 (2H, m), 7.66 (1H, m), 7.58 (2H, m), 5.22 (1H, dd, J=3.2 Hz, 8.0 Hz), 4.98 (1H, s), 4.90 (1H, s), 4.15 (1H, m), 4.12 (2H, m), 3.82 (2H, m), 3.73 (2H, m), 3.44-3.57 (4H, m), 3.44 (1H, d, J=10.4 Hz), 3.38 (1H, d, J=10.4 Hz), 3.37 (3H, s), 3.12 (1H, dd, J=4.0 Hz, 14.0 Hz), 2.96 (1H, dd, J=10.4 Hz, 14.0 Hz), 2.63 (1H, m), 2.46 (1H, dd, J=8.8 Hz, 13.6 Hz), 2.37 (1H, dd, J=6.8 Hz, 13.6 Hz), 2.11 (1H, m), 2.04 (3H, s), 1.92 (2H, m), 1.45-1.85 (12H, m), 1.16 (9H, s), 1.01 (3H, d, J=6.8 Hz), 0.85 (18H, s), 0.06 (6H, s), 0.02 (6H, s); $^{13}C$ NMR (100 MHz, $CDCl_3$): δ 178.74, 170.37, 152.99, 139.98, 134.14, 129.69 (2C), 128.08 (2C), 110.14, 85.58, 81.24, 81.07, 78.42, 76.39, 75.54, 73.52, 71.47, 68.96, 68.01, 64.27, 57.97, 57.56, 43.88, 43.82, 39.94, 38.94, 37.83, 33.54, 33.40, 32.72, 28.13, 27.43 (3C), 26.21 (3C), 26.17 (3C), 25.51, 25.03, 22.21, 21.56, 20.29, 18.59, 18.38, −3.87, −4.48, −5.09 (2C).

Zinc powder (1.54 g, 23.6 mmol, 50 eq) was suspended in water (1.1 ml) and cooled to 0° C. AcOH (0.40 ml, 7.1 mmol, 15 eq) was added at 0° C. A solution of Compound AF (530 mg, 0.473 mmol, 1 eq) in THF (2.7 ml) was added at 0° C., and the mixture was allowed to warm to 20° C. After 3 h, the reaction mixture was filtered for removal of zinc powder. The reactor was rinsed with a mixture of THF (1.1 ml) and water (1.1 ml). The filtrate was diluted with MTBE (10.6 ml), sequentially washed with: 1) 20 wt % Rochelle salt (aqueous solution, 2.7 g, 4.0 eq), 2) saturated $NaHCO_3$ (6.0 g), and 3) 20 wt % NaCl (aqueous solution, 2.6 g), and concentrated to give crude product as colorless oil. The crude was purified by Biotage (Uppsala, Sweden) 25M (heptane-MTBE 1:1 v/v) to give Compound AE (393 mg, 0.394 mmol, 83% yield) as colorless oil. $^1H$ NMR (400 MHz, $CDCl_3$): δ 7.93 (2H, m), 7.66 (1H, m), 7.58 (2H, m), 5.23 (1H, t, J=6.4 Hz), 5.05 (1H, s), 4.95 (1H, d, J=1.6 Hz), 4.88 (1H, s), 4.83 (1H, d, J=1.6 Hz), 4.33 (1H, br), 4.02 (3H, m), 3.83 (2H, m), 3.76 (1H, m), 3.60 (1H, m), 3.54 (1H, dd, J=5.6 Hz, 10.4 Hz), 3.47 (2H, m), 3.37 (3H, s), 3.15 (1H, dd, J=4.0 Hz, 14.0 Hz), 2.95 (1H, dd, J=10.0 Hz, 14.0 Hz), 2.83 (1H, d, J=5.2 Hz), 2.65 (2H, m), 2.40 (1H, m), 2.23 (1H, m), 2.03 (3H, s), 1.96-2.03 (2H, m), 1.81 (1H, m), 1.67-1.80 (3H, m), 1.40-1.67 (7H, m), 1.17 (9H, s), 1.01 (3H, d, J=6.8 Hz), 0.86 (18H, s), 0.06 (6H, s), 0.03 (6H, s); $^{13}C$ NMR (100 MHz, $CDCl_3$): δ 178.80, 170.77,

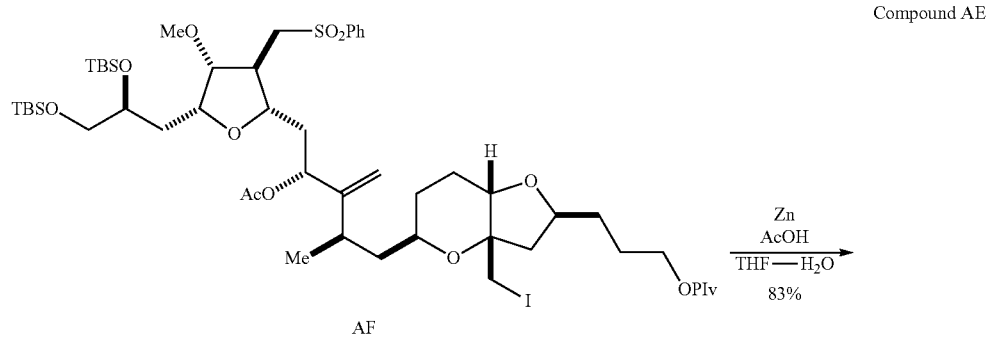

AF

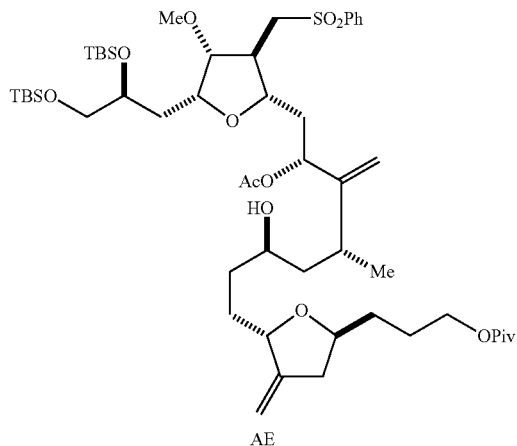

Compound AE

AE 153.18, 151.49, 139.77, 134.16, 129.67 (2C), 128.16 (2C), 109.77, 105.27, 85.84, 80.92, 80.15, 78.57, 76.97, 74.59, 71.51, 68.80, 68.05, 64.43, 58.01, 57.56, 45.21, 43.49, 39.78, 38.94, 34.58, 33.55, 32.28, 31.77, 31.74, 27.42 (3C), 26.21 (3C), 26.17 (3C), 25.49, 22.78, 21.51, 18.60, 18.39, −3.87, −4.51, −5.11 (2C).

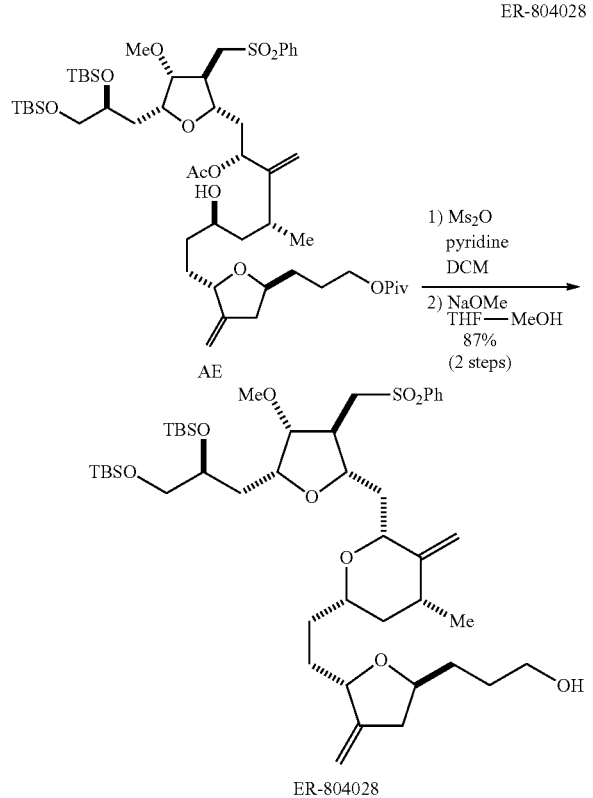

Compound AE (280 mg, 0.281 mmol, 1 eq) was dissolved in CH$_2$Cl$_2$ and cooled to 0° C. Pyridine (0.045 ml, 0.56 mmol, 2.0 eq) was added followed by Ms$_2$O (58.8 mg, 0.338 mmol, 1.20 eq). The reaction was allowed to warm to room temperature, and stirring was continued for an additional 1 h. The reaction mixture was cooled to 0° C., diluted with MTBE (5.6 ml), washed with saturated NaHCO$_3$ (0.84 g), and concentrated to give crude product as colorless film. The crude was azeotropically dried with heptane (3 ml×2) and re-dissolved in THF (7.0 ml). The mixture was cooled to 0° C. and treated with 25 wt % NaOMe (0.13 ml). After 10 min, the reaction was allowed to warm to room temperature, and stirring was continued for an additional 30 min. The mixture was treated with additional 25 wt % NaOMe (0.045 ml), and stirring was continued for an additional 20 min. The reaction mixture was diluted with heptane (7.0 ml) and washed with water (1.4 ml). The organic layer was separated, sequentially washed with: 1) 20 wt % NH$_4$Cl (0.84 g) and 2) 20 wt % NaCl (3 g), and concentrated to give crude product as brownish oil. The crude was purified by Biotage (Uppsala, Sweden) 12M (heptane-MTBE 2:3 v/v) to give ER-804028 (209 mg, 0.245 mmol, 87%) as pale yellow oil. $^1$H NMR (400 MHz, CDCl$_3$): δ 7.89 (2H, m), 7.64 (1H, m), 7.56 (2H, m), 4.85 (1H, d, J=1.6 Hz), 4.80 (1H, s), 4.72 (1H, s), 4.61 (1H, d, J=1.6 Hz), 4.23 (1H, br), 3.91 (1H, m), 3.79 (1H, m), 3.76 (2H, m), 3.63 (1H, m), 3.50-3.60 (4H, m), 3.43 (1H, dd, J=5.6 Hz, 10.0 Hz), 3.38 (3H, s), 3.32 (1H, m), 2.98 (2H, m), 2.61 (1H, br), 2.56 (1H, m), 2.50 (1H, m), 2.08-2.22 (3H, m), 1.96 (1H, m), 1.84 (1H, m), 1.78 (1H, m), 1.70 (1H, m), 1.42-1.63 (6H, m), 1.28-1.42 (2H, m), 1.01 (3H, d, J=6.8 Hz), 0.84 (18H, s), 0.05 (3H, s), 0.04 (3H, s), 0.00 (3H, s), −0.01 (3H, s); and $^{13}$C NMR (100 MHz, CDCl$_3$): δ 150.34, 150.75, 139.91, 134.18, 129.73 (2C), 128.14 (2C), 105.10, 85.97, 80.92, 79.72, 78.50, 77.45, 77.09, 75.53, 71.59, 68.04, 62.88, 58.27, 57.73, 43.51, 42.82, 39.16, 37.68, 35.69, 33.31, 32.41, 31.89, 31.48, 29.79, 26.21 (3C), 26.17 (3C), 18.58, 18.38, 18.13, −3.85, −4.71, −5.12 (2C).

Alternate Route to Compound W

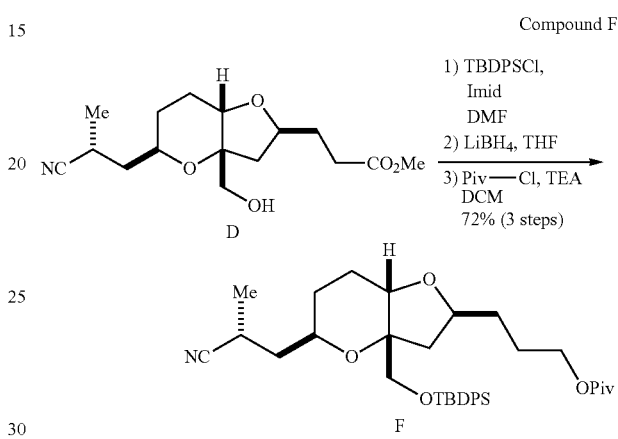

Compound D (0.657 g, 2.11 mmol, 1 eq) was dissolved in DMF (1.3 ml) and cooled to 0° C. Imidazole (0.287 g, 4.22 mmol, 2.00 eq) was added, followed by TBDPSCl (0.576 ml, 2.22 mmol, 1.05 eq). The mixture was stirred at 0-5° C. for 1 h and allowed to warm to room temperature. After stirring overnight (16 h), the reaction mixture was diluted with water (5.2 ml) and extracted with MTBE (5.2 ml). The organic layer was separated and set aside. The aqueous layer was extracted with MTBE (5.2 ml). All organic layers were combined, washed with water (2.6 ml), and concentrated to give crude Compound X:

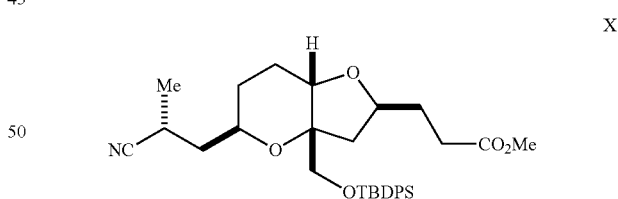

as pale yellow oil. Compound X (2.11 mmol assumed, 1 eq) was dissolved in toluene (4.6 ml) and cooled to −5° C. 2.0 M LiBH$_4$ (solution in THF, 2.43 ml, 4.85 mmol, 2.30 eq) was added while maintaining T-internal <0° C. A mixture of MeOH (0.196 ml, 4.85 mmol, 2.30 eq) and toluene (0.80 ml) was added at <0° C., and then reaction was allowed to warm to 20-22° C. After 22 h, the reaction mixture was carefully/slowly poured into a pre-chilled (0° C.) mixture of 20 wt % citric acid (aqueous solution, 6.0 g, 6.2 mmol, 3.0 eq) and MTBE (20 ml) while maintaining T-internal <10° C. The organic layer was separated, sequentially washed with: 1) saturated NaHCO$_3$ (3.0 g) and 2) water (3.0 g), and concentrated to give crude Compound Y:

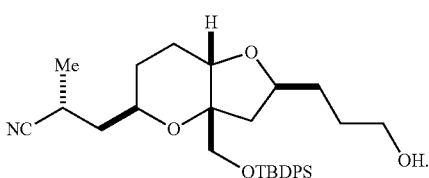

Compound Y (2.11 mmol assumed, 1 eq) was dissolved in CH$_2$Cl$_2$ (2.5 ml) at room temperature. TEA (0.441 ml, 3.16 mmol, 1.50 eq) was added followed by DMAP (26 mg, 0.21 mmol, 0.10 eq). The mixture was cooled to 0° C. and treated with pivaloyl chloride (0.272 ml, 2.22 mmol, 1.05 eq). The reaction was allowed to warm to room temperature and stirring was continued overnight (16 h). The reaction mixture was diluted with MTBE (10 ml), sequentially washed with: 1) 20 wt % citric acid (aqueous solution, 3.0 g, 1.5 eq) and 2) saturated NaHCO$_3$ (aqueous solution, 3.0 g), and concentrated to give crude product as orange-colored oil. The crude was purified by Biotage (Uppsala, Sweden) 25M (heptane-MTBE 7:3 v/v) to give Compound F (0.920 g, 1.52 mmol, 72% overall yield) as colorless oil.

whole biphasic mixture was filtered for removal of Zn. The reactor and Zn were rinsed with MTBE (9 ml). The organic layer was separated, sequentially washed with: 1) saturated NaHCO$_3$ (aqueous solution, 3.8 g) and 2) 20 wt % NaCl (2.7 g), and concentrated to give crude Compound I as pale yellow oil. Compound I (1.50 mmol assumed, 1 eq) was suspended in THF (2.5 ml)-water (1.5 ml) and treated with AcOH (4.5 ml, 7.9 mmol) at room temperature for 2 h. The reaction mixture was diluted with toluene (20 ml) and concentrated. The same operation was repeated with toluene (20 ml×2) to give crude Compound Z:

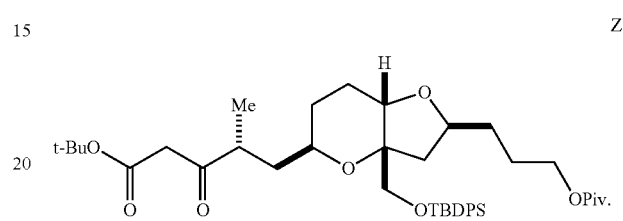

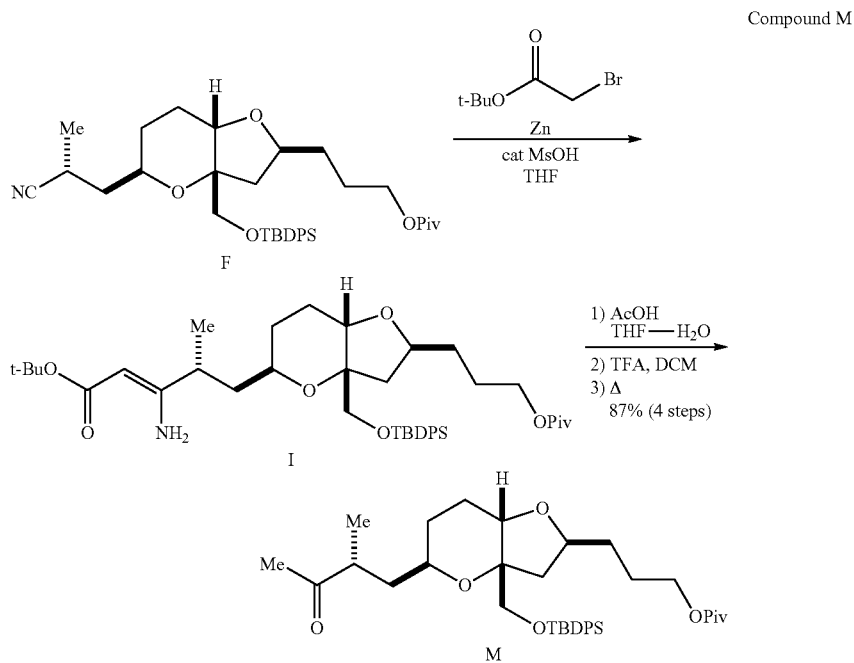

Zinc dust (982 mg, 15.0 mmol, 10.0 eq) was suspended in THF (1.8 ml), and MsOH (0.0097 ml, 0.15 mmol, 0.10 eq) was added. The resultant mixture was heated at reflux for 30 min and then cooled to 20° C. A solution of Compound F (910 mg, 1.50 mmol, 1 eq) and t-butyl bromoacetate (0.222 ml, 15.0 mmol, 1.00 eq) in THF (4.6 ml) was added, and the mixture was heated at reflux. After 2 h, t-butyl bromoacetate (0.222 ml, 1.50 mmol, 1.00 eq) was added, and heating was continued for 4 h. t-Butyl bromoacetate (0.111 ml, 1.50 mmol, 0.50 eq) was added, and heating was continued for an additional 6 h. After cooling down, the reaction mixture was diluted with MTBE (14 ml) and cooled to 0° C. 20 wt % citric acid (aqueous solution, 7.2 g, 7.5 mmol, 5.0 eq) was added at <10° C., and vigorous stirring was continued for 10 min. The The crude was purified by Biotage (Uppsala, Sweden) 25M (heptane-MTBE 4:1 v/v) to give Compound Z (1.062 g, 1.47 mmol, 97% yield) as colorless oil.

Compound Z (1.00 g, 1.38 mmol, 1 eq) was dissolved in CH$_2$Cl$_2$ (9.0 ml) and treated with TFA (1.00 ml, 13.0 mmol) at room temperature. After 4 h, the reaction mixture was diluted with toluene (15 ml) and concentrated. The same operation was repeated with toluene (15 ml×2) to give crude Compound K. Compound K was dissolved in toluene (10 ml), heated at 100° C. for 30 min, and concentrated to give crude Compound M. The crude was purified by Biotage (Uppsala, Sweden) 25M (heptane-MTBE 7:3 v/v) to give Compound M (775 mg, 1.24 mmol, 90% yield) as colorless oil.

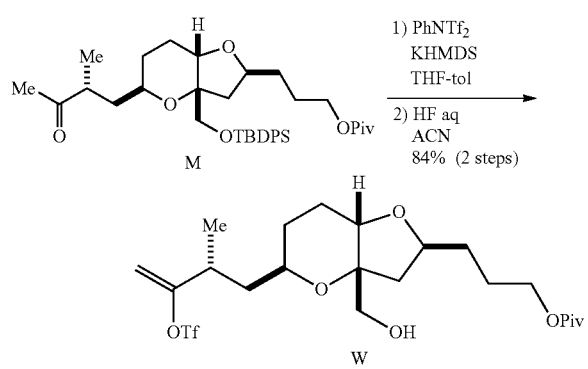

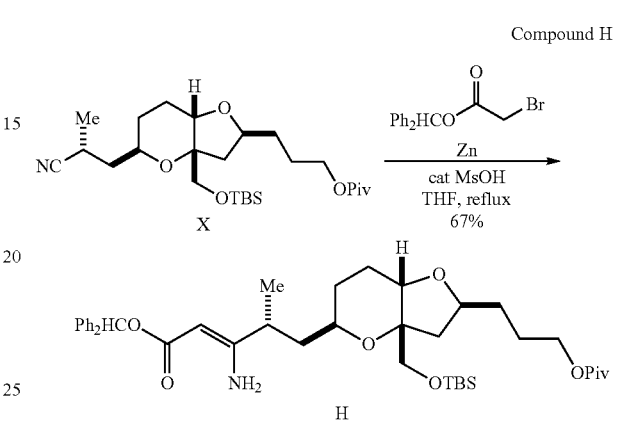

Compound M (745 mg, 1.20 mmol, 1 eq) was dissolved in THF (4.5 ml) and PhNTf$_2$ (641 mg, 1.79 mmol, 1.50 eq) was added at 20° C. Upon complete dissolution of PhNTf$_2$, the mixture was cooled to −23° C. 0.5 M KHMDS (solution in toluene, 2.63 ml, 1.32 mmol, 1.10 eq) was added while maintaining T-internal <−18° C., and the mixture was stirred at −18 to −20° C. for 1 h. Under vigorous stirring, 20 wt % NH$_4$Cl (aqueous solution, 0.32 g) was added while maintaining T-internal <−10° C., and then the mixture was allowed to warm to 0° C. The mixture was diluted with MTBE (7.5 ml) and water (0.74 ml), and vigorous stirring was continued for 5 min. The organic layer was separated, washed with water (1.5 ml), and concentrated to give crude Compound AA:

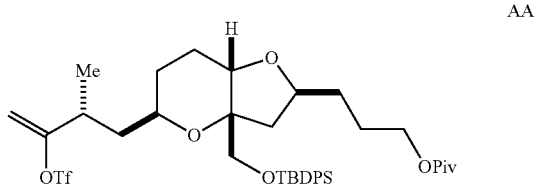

as yellow solid-oil. Compound AA was dissolved in CH$_3$CN (9.0 ml) and treated with 49 wt % HF (aqueous solution, 3.0 g) at room temperature for 20 h. The reaction mixture was carefully/slowly poured into a pre-chilled (0° C.) mixture of MTBE (40 ml), water (7.5 ml), and NaHCO$_3$ (8.5 g) while maintaining T-internal <10° C. The organic layer was separated and set aside. The aqueous layer was extracted with MTBE (7.5 ml). All organic layers were combined, washed with 20 wt % NaCl (aqueous solution, 3.7 g), and concentrated to give crude Compound W as yellow solid-oil. The crude was purified by Biotage (Uppsala, Sweden) 25M (heptane-MTBE 1:1 & 2:3 v/v) to give Compound W (522 mg, 1.01 mmol, 84% yield) as pale yellow oil.

Alternate Route to Compound L

Zinc (1.06 g, 16.2 mmol, 10 eq) was suspended in THF (2.3 ml). MsOH (0.010 ml, 0.02 mmol, 0.1 eq) was added at room temperature, and the resultant slurry was heated at reflux for 30 min. After cooling down, a mixture of Compound X (780 mg, 1.62 mmol, 1 eq) and benzhydryl bromoacetate (0.74 g, 2.4 mmol, 1.5 eq; Kume et al., *Tetrahedron*, 1997, 53, 1635) in THF (3.9 ml) was added, and the reaction was heated to reflux. After heating for 3 h, benzhydryl bromoacetate (0.74 g, 2.4 mmol, 1.5 eq) was added, and heating was continued for an additional 7 h. After cooling down, the mixture was diluted with MTBE (16 ml) and filtered through a pad of Celite (1.6 g). The filtrate was sequentially washed with: 1) 20 wt % citric acid (aqueous solution, 3.9 g), 2) 10 wt % NaHCO$_3$ (aqueous solution, 3.9 g), and 3) 20 wt % NaCl (aqueous solution, 2.3 g), and concentrated to give crude product as yellow oil. The crude was purified by Biotage (Uppsala, Sweden) 40M (heptane-MTBE 1:1 v/v) to give Compound H as pale yellow oil (770 mg, 1.08 mmol, 67% yield).

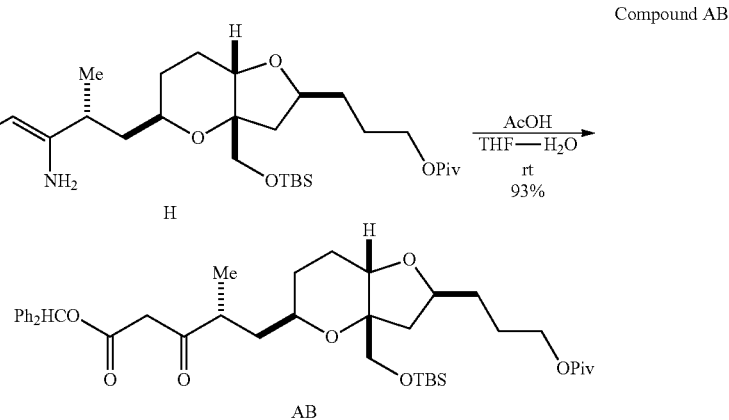

Compound H (770 mg, 1.08 mmol, 1 eq) was dissolved in THF (0.77 ml) and cooled to 0° C. Water (0.38 ml) was added followed by AcOH (1.54 ml). The mixture was allowed to warm to room temperature, and stirring was continued for 8 h. The reaction mixture was diluted with toluene (15 ml) and concentrated. The residue was further azeotroped with toluene (15 ml×2) and purified by Biotage (Uppsala, Sweden) 25M (heptane-MTBE 2:1 v/v) to give Compound AB (716 mg, 1.01 mmol, 93% yield) as pale yellow oil.

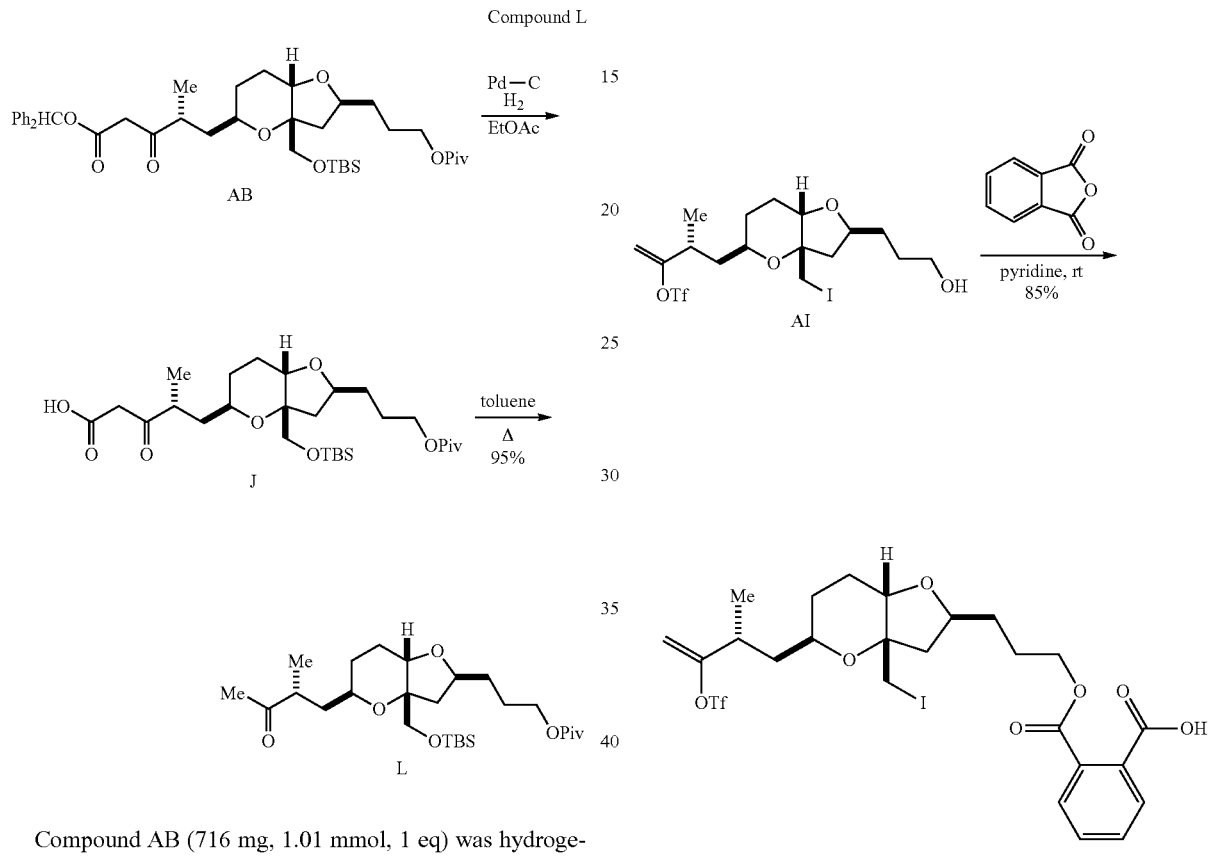

Compound AB (716 mg, 1.01 mmol, 1 eq) was hydrogenated with 10 wt % Pd—C (wet-type, 0.11 g, 0.050 mmol, 0.05 eq), H$_2$ (balloon), and EtOAc (7.2 ml) for 2 h. The reaction mixture was filtered, concentrated, and re-dissolved in toluene (7.2 ml). The mixture was heated at 100° C. for 15 min. After cooling down, the mixture was concentrated and purified by Biotage (Uppsala, Sweden) 25M (heptane-MTBE 2:1 v/v) to give Compound L (476 mg, 0.954 mmol, 95% yield) as colorless oil.

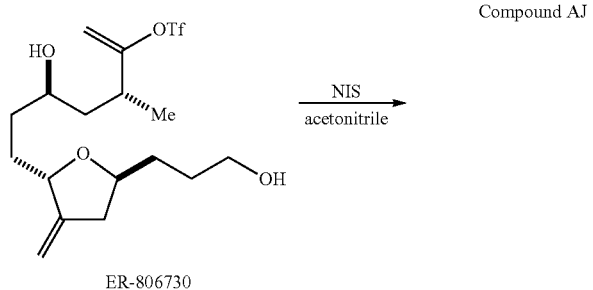

Compound AI was synthesized from ER-806730 (WO 2005/118565, Example 2) by iodo-etherification with N-iodosuccinimide in acetonitrile.

Compound AI (2.95 g, 5.44 mmol, 1 eq) was dissolved in pyridine (3.0 ml, 36 mmol, 6.7 eq) and treated with phthalic anhydride (0.846 g, 5.71 mol, 1.05 eq) at room temperature for 18 h. The reaction mixture was diluted with MTBE (200 ml), sequentially washed with: 1) 20 wt % citric acid (35 g); 2) 20 wt % citric acid (35 g); 3) water (9 g); and 4) water (9 g), and concentrated to give crude product as pale yellow oil. The crude was purified by Biotage (Uppsala, Sweden) 25M (heptane-MTBE 1:1 & MTBE 100%) to give Compound AJ as colorless oil (3.20 g, 4.63 mmol, 85% yield). $^1$H NMR (400 MHz, CDCl$_3$): δ 7.83 (1H, m), 7.71 (1H, m), 7.53-7.59 (2H, m), 5.08 (1H, d, J=3.6 Hz), 5.01 (1H, d, J=3.6 Hz), 4.51 (1H, m), 4.27 (1H, m), 4.20 (1H, m), 3.87 (1H, dd, J=6.0 Hz, 9.2 Hz), 3.54 (1H, m), 3.50 (1H, d, J=10.8 Hz), 3.48 (1H, d, J=10.8 Hz), 2.84 (1H, m), 2.33 (1H, dd, J=8.8 Hz, 13.6 Hz), 1.83-1.94 (2H, m), 1.46-1.80 (8H, m), 1.22 (1H, m), 1.13 (3H, d, J=6.8 Hz).

Compound AK

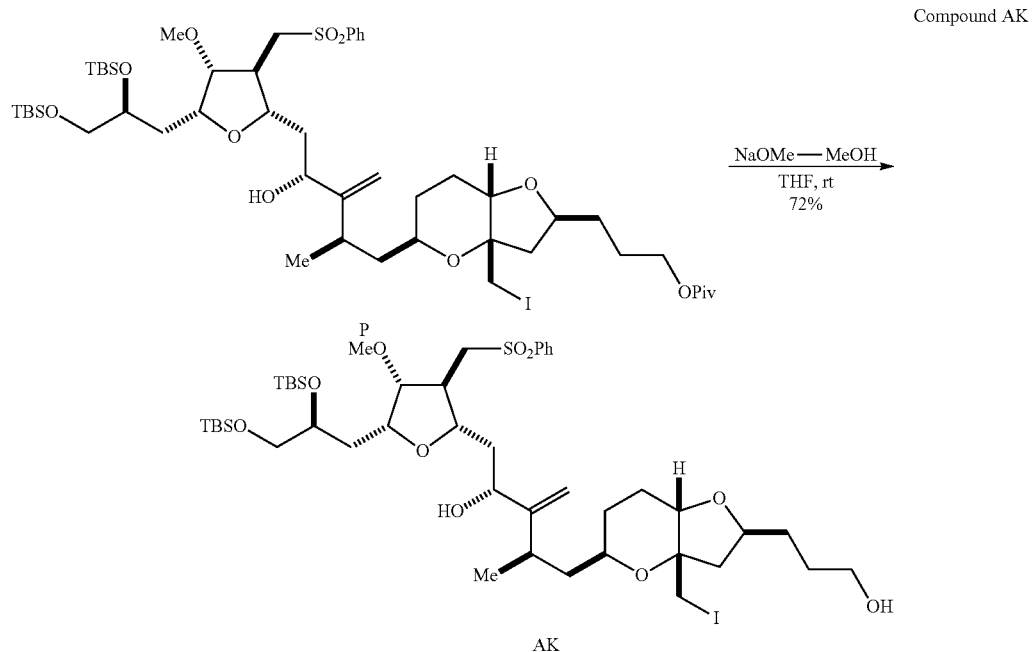

Compound P (0.050 g, 0.046 mmol, 1 eq) was dissolved in THF (0.30 mL) and treated with NaOMe (25 wt % solution in MeOH, 0.10 ml, 0.44 mmol, 9.4 eq) at room temperature for 1 h. The reaction mixture was diluted with MTBE (3.0 ml), sequentially washed with: 1) water (0.30 g); 2) water (0.30 g); and 3) 20 wt % NaCl (0.30 g), and concentrated to give crude product as colorless oil. The crude product was purified by preparative TLC (MTBE 100%) to give Compound AK as colorless film (33 mg, 0.033 mmol, 72% yield).

Compounds AL and AM

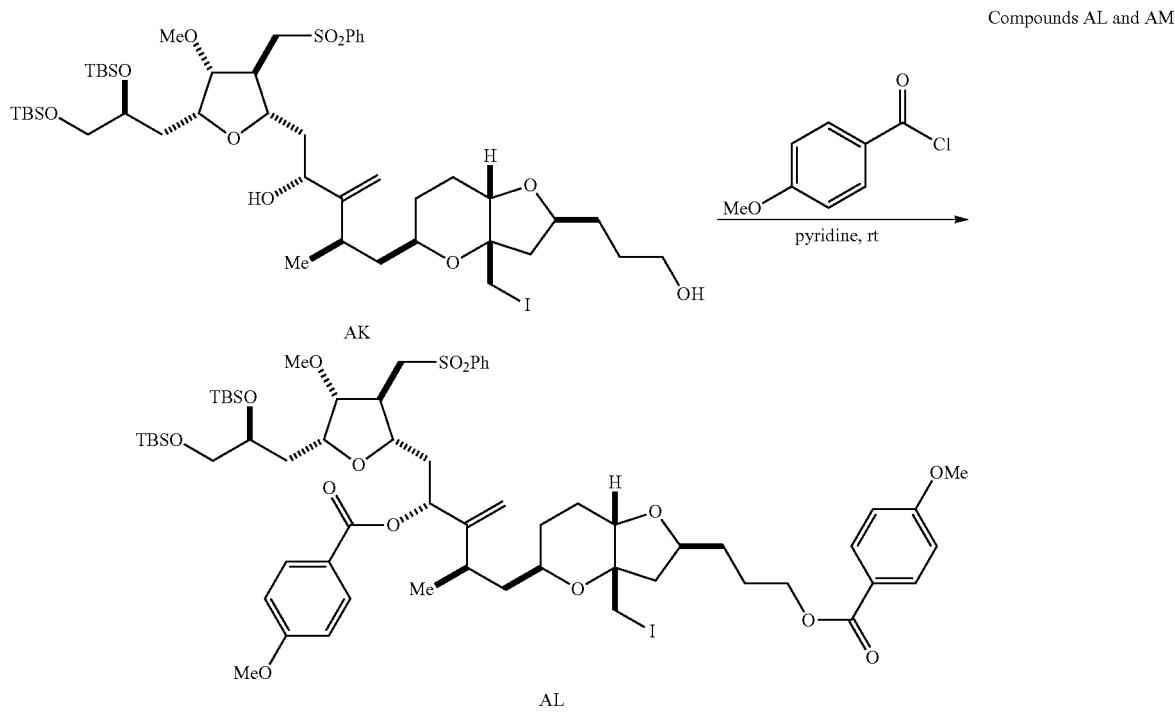

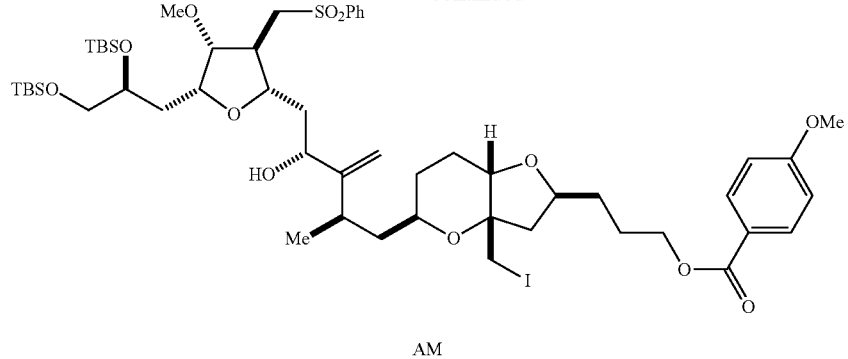

AM

Compound AK (0.175 g, 0.176 mmol, 1 eq) was dissolved in pyridine (0.56 ml, 6.9 mmol, 39 eq). 4-methoxybenzoyl chloride (0.066 g, 0.39 mmol, 2.2 eq) was added at room temperature, and the mixture was stirred for 15 h. The reaction mixture was diluted with MTBE (7 ml) and washed with 20 wt % citric acid (7 g). The organic layer was separated and set aside. The aqueous layer was extracted with MTBE (7 ml). All organic layers were combined, sequentially washed with 20 wt % citric acid (3 g) and water (3 g), and concentrated to give crude product as pale yellow oil. The crude product was purified by Biotage (Uppsala, Sweden) 12M KP-Sil (heptane-MTBE 7:3 & 1:1) to give Compound AL (0.02 g, 0.02 mmol, 9% yield, colorless film) and Compound AM (0.14 g, 0.12 mmol, 70% yield, colorless oil). Compound AM: $^1$H NMR (400 MHz, CDCl$_3$) δ 7.95 (2H, d, J=8.8 Hz), 7.89 (2H, d, J=7.2 Hz), 7.65 (1H, m), 7.57 (2H, m), 6.87 (2H, d, J=8.8 Hz), 5.18 (1H, s), 4.85 (1H, s), 4.26 (2H, m), 4.20 (1H, m), 4.12 (1H, m), 3.92 (1H, m), 3.83 (3H, s), 3.70-3.80 (3H, m), 3.53 (1H, m), 3.40-3.50 (4H, m), 3.36 (3H, s), 3.08 (2H, m), 2.57 (1H, m), 2.38 (1H, dd, J=9.2 Hz, 14 Hz), 2.29 (1H, m), 1.98 (1H, m), 1.71-1.92 (7H, m), 1.52-1.68 (7H, m), 1.48 (1H, m), 1.18 (1H, m), 1.04 (3H, d, J=7.2 Hz), 0.86 (9H, s), 0.84 (9H, s), 0.05 (6H, s), 0.02 (3H, s), 0.01 (3H, s).

Synthesis of Compound AD and Synthesis of Compound P from Compound AD

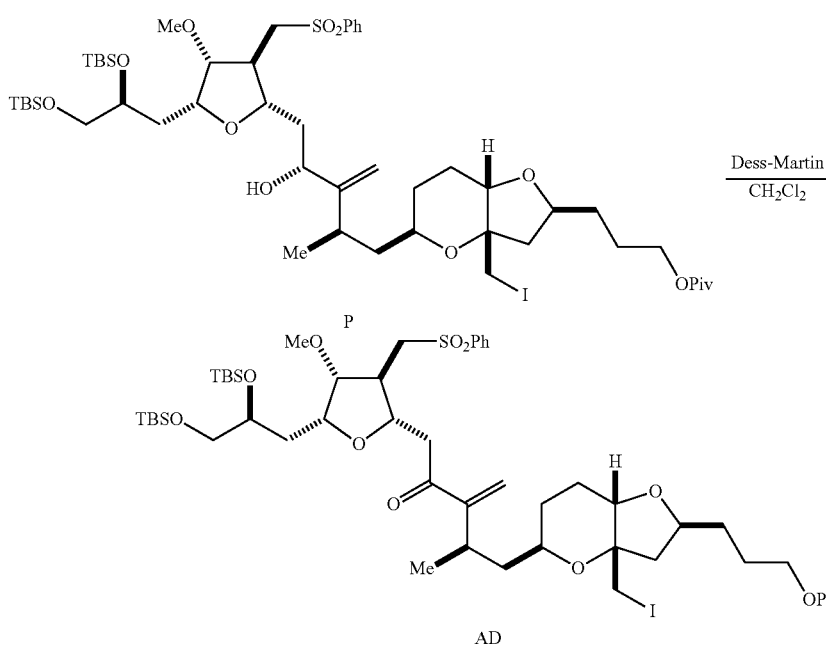

Compound AD was prepared in the process of producing a mixture of Compound P with its C27 diastereomer. Compound P (50.2 mg, 0.0465 mmol, 1 eq) was dissolved in CH$_2$Cl$_2$ (0.50 ml). Dess-Martin periodinane (23.6 mg, 0.0556 mol, 1.2 eq) was added at room temperature. After 10 min, NaHCO$_3$ (40 mg, 0.5 mmol) was added followed by isopropyl alcohol (0.014 ml, 0.19 mol, 4 eq), and stirring was continued for an additional 1 h. The mixture was diluted with MTBE (2 ml), washed with water (0.5 ml), and concentrated to give crude product as a colorless oil. The crude was purified by Biotage (Uppsala, Sweden) 12M (heptane-MTBE 7:3 & 1:1) to give Compound AD (42 mg, 0.039 mmol, 84% yield) as a colorless oil. $^1$H NMR (400 MHz, CDCl$_3$): δ 7.92 (2H, m), 7.63 (1H, m), 7.56 (2H, m), 5.96 (1H, s), 5.74 (1H, s), 4.15 (1H, m), 4.04 (2H, m), 3.94 (1H, d, J=3.2 Hz), 3.89 (2H, m), 3.75 (2H, m), 3.54 (2H, m), 3.39 (3H, s), 3.44 (1H, m), 3.43 (1H, d, J=10.4 Hz), 3.34 (1H, d, J=10.4 Hz), 3.19 (1H, m), 3.02 (1H, dd, J=10.8 Hz, 14 Hz), 2.98 (1H, dd, J=8.0 Hz, 17.2 Hz), 2.81 (1H, m), 2.42 (1H, m), 2.31 (1H, dd, J=8.8 Hz, 14 Hz), 1.98 (1H, m), 1.45-1.85 (12H, m), 1.17 (9H, s), 1.02 (3H, d, J=7.2 Hz), 0.87 (9H, s), 0.86 (9H, s), 0.07 (3H, s), 0.06 (3H, s), 0.03 (3H, s), 0.02 (3H, s).

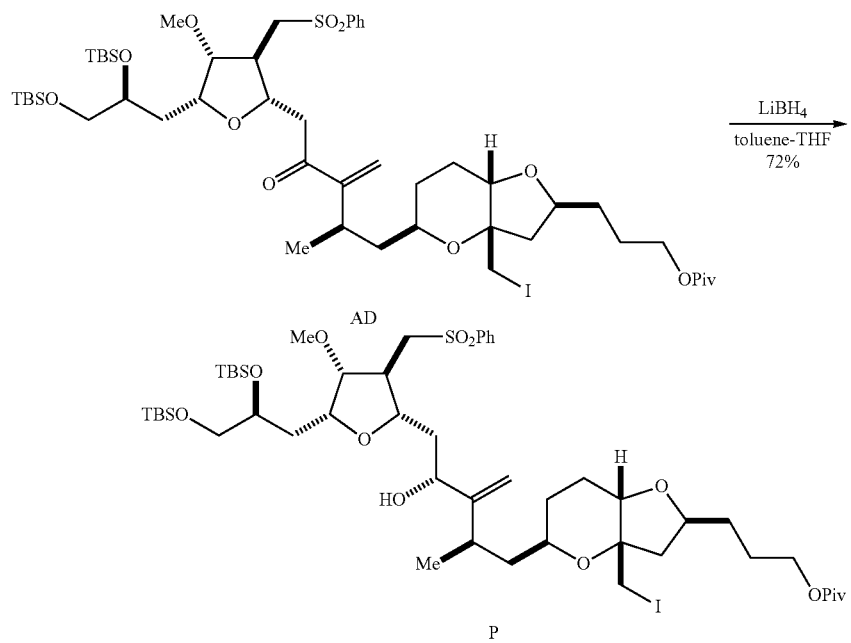

Compound P can also be obtained from reduction of Compound AD, made by any means. Compound AD (33 mg, 0.031 mmol) was dissolved in toluene (0.50 ml) and cooled to 0° C. 2.0 M LiBH$_4$ (solution in THF, 8 μl) was added at 0° C., and stirring was continued at 0° C. for 10 min. 2.0 M LiBH$_4$ (solution in THF, 8 μl) was added, and stirring was continued for an additional 10 min The reaction mixture was diluted with MTBE (1.0 ml), sequentially washed with 20 wt % citric acid (aqueous solution, 0.20 g) and saturated NaHCO$_3$ (aqueous solution, 0.20 g), and concentrated to give crude product. The crude was purified by preparative TLC (heptane-MTBE 2:3) to give Compound P (24 mg, 72% yield, C27-dr 5:1).

Other Embodiments

All publications, patents, and patent application publications mentioned herein are hereby incorporated by reference. Various modifications and variations of the described compounds of the invention will be apparent to those skilled in the art without departing from the scope and spirit of the invention. Although the invention has been described in connection with certain embodiments, it should be understood that the invention as claimed should not be unduly limited to such embodiments. Indeed, various modifications of the described modes for carrying out the invention that are obvious to those skilled in the relevant art are intended to be within the scope of the invention.

What is claimed is:
1. A method of synthesizing ER-804028:

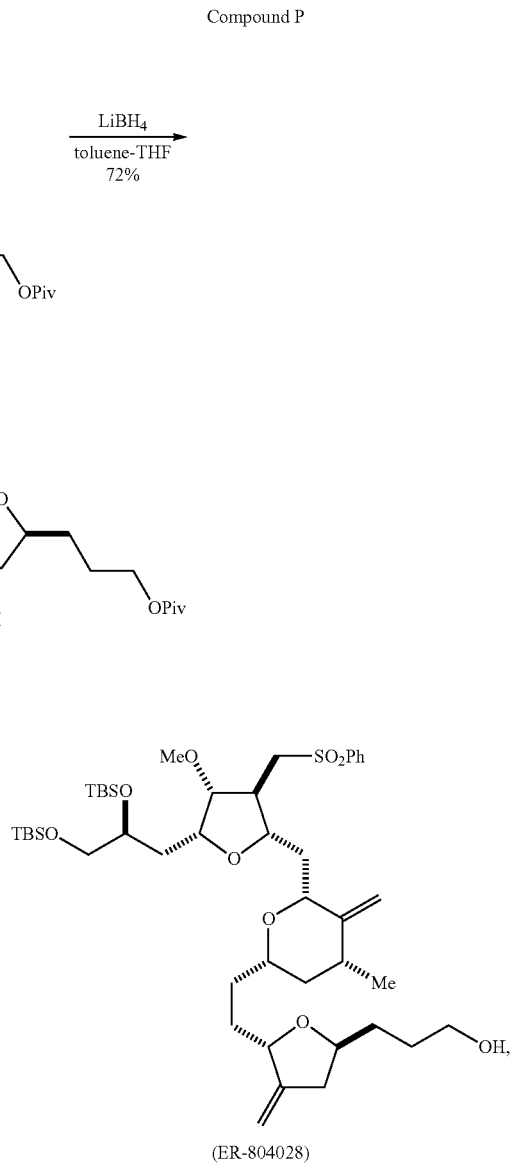

said method comprising the steps of:
(i) reacting a compound having the formula (I):

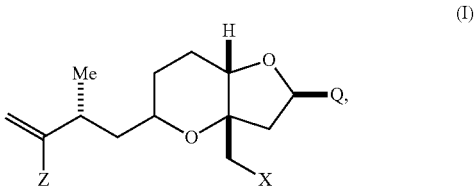

wherein X is halogen or oxo; Z is a leaving group; Q is —C(O)H, —CH═CHC(O)OY$_1$, —C(R)H(CH$_2$)$_n$OY$_1$, or —C(R)HCH$_2$C(O)OY$_1$; R is H or —OY$_2$; Y$_1$ and Y$_2$ are each independently H or a hydroxyl protecting group; and n is 1 or 2 with a compound having the formula (IV):

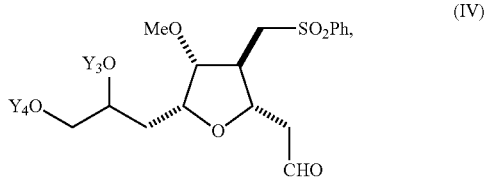

(IV)

wherein Y$_3$, and Y$_4$, are each independently H or a hydroxyl protecting group, under NHK coupling conditions to produce a compound having the formula:

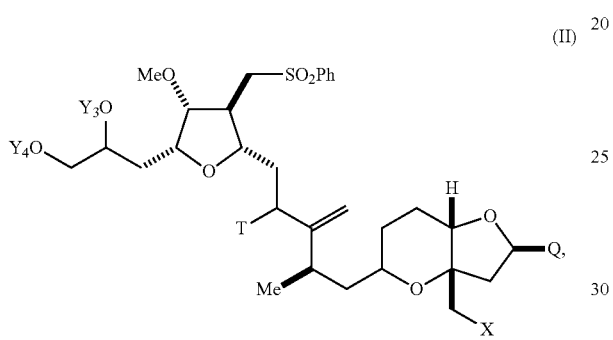

(II)

wherein X is halogen or oxo; Q is —C(O)H, —CH═CHC(O)OY$_1$, —C(R)H(CH$_2$)$_n$OY$_1$, or —C(R)HCH$_2$C(O)OY$_1$; R is H or —OY$_2$; n is 1 or 2; Y$_1$, Y$_2$, Y$_3$, and Y$_4$ are each independently H or a hydroxyl protecting group; T is oxo or —OY$_5$; and Y$_5$ is H or a hydroxyl protecting group, or Y$_5$, together with the oxygen atom to which it is bound, is a leaving group;

(ii) reacting the product of step (i) under Vasella fragmentation conditions to produce a compound having the formula:

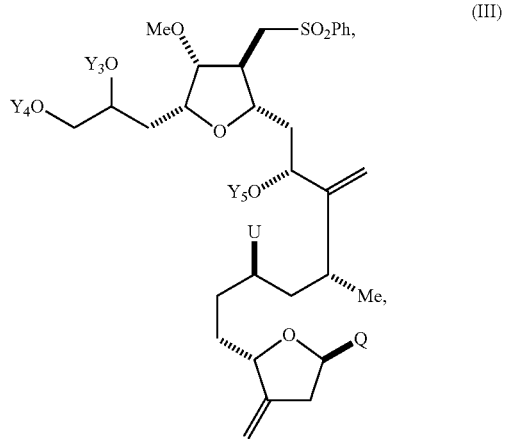

(III)

wherein Q is —C(O)H, —CH═CHC(O)OY$_1$, —C(R)H(CH$_2$)$_n$OY$_1$, or —C(R)HCH$_2$C(O)OY$_1$; R is H or —OY$_2$; n is 1 or 2; Y$_1$, Y$_2$, Y$_3$, and Y$_4$ are each independently H or a hydroxyl protecting group; U is —OY$_6$; Y$_5$ is H or a hydroxyl protecting group or Y$_5$, together with the oxygen atom to which it is bound, is a leaving group; and Y$_6$ is H or a hydroxyl protecting group or Y$_6$, together with the oxygen atom to which it is bound, is a leaving group, provided that when Q is —(CH$_2$)$_3$OY$_1$, —OY$_6$ is a leaving group, and Y$_1$, Y$_3$, and Y$_4$ are protecting groups, Y$_5$ is not H; and (iii) reacting the product of step (ii) under conditions for intramolecular Williamson etherification to produce ER-804028.

2. The method of claim 1, wherein the compound of formula (I) has formula (Ia):

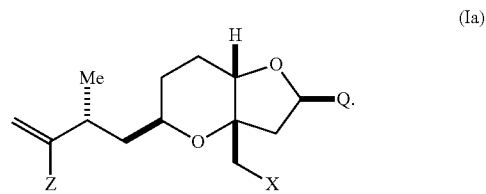

(Ia)

3. The method of claim 1, wherein Q is —(CH$_2$)$_3$OY$_1$.

4. The method of claim 1, wherein, in the compound of formula (I), Y$_1$, together with the oxygen to which it is bound, is an ester, carbonate, carbamate, sulfonate, or ether hydroxyl protecting group.

5. The method of claim 4, wherein, in the compound of formula (I), Y$_1$ is pivaloyl, acetyl, benzoyl, p-bromobenzoyl, p-methoxybenzoyl, 1-naphthoyl, 2-naphthoyl, o-phthaloyl, benzyl, p-methoxybenzyl, triphenylmethyl, tri(C1-C6 alkyl)silyl, tri(C6-C10 aryl or C1-C6 heteroaryl)silyl, di(C6-C10 aryl or C1-C6 heteroaryl)(C1-C6 alkyl)silyl, or (C6-C10 aryl or C1-C6 heteroaryl)di(C1-C6 alkyl)silyl.

6. The method of claim 1, wherein X is halogen.

7. The method of claim 1, wherein Z is halogen or (C1-C6) alkylsulfonate.

8. The method of claim 7, wherein Z is triflate, iodide, or bromide.

9. The method of claim 1, wherein the compound of formula (I) has formula (Ib):

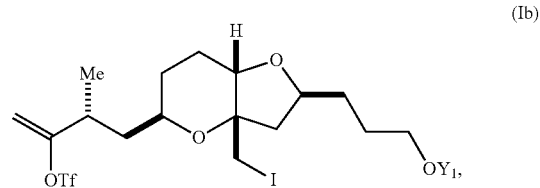

(Ib)

wherein Y$_1$ is H, pivaloyl, benzoyl, p-bromobenzoyl, 1-naphthoyl, 2-naphthoyl, p-methoxybenzoyl, or o-phthaloyl or a salt thereof.

10. The method of claim 1, wherein the compound of formula (II) has formula (IIa):

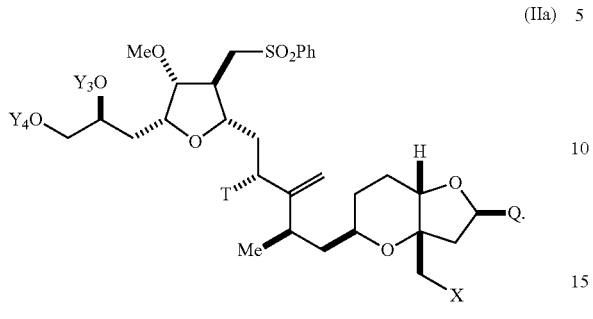

11. The method of claim 1, wherein the compound of formula (II) has formula (IIb):

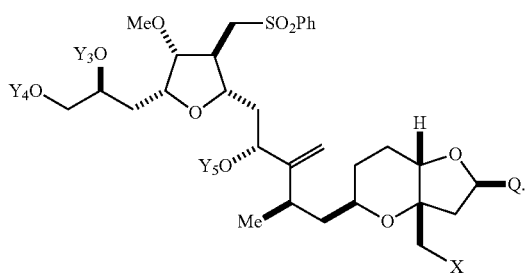

12. The method of claim 1, wherein, in the compound of formula (II), Q is —(CH$_2$)$_3$ OY$_1$;
- Y$_1$, together with the oxygen atom to which it is bound, is an ester, carbonate, carbamate, sulfonate, or ether hydroxyl protecting group;
- each of Y$_3$ and Y$_4$ is, independently and together with the oxygen atom to which it is bound, an ester, carbonate, carbamate, sulfonate, or ether hydroxyl protecting group, or Y$_3$ and Y$_4$ together with the oxygen atoms to which they are bound are a cyclic carbonate, cyclic boronate, or cyclic silylene hydroxyl protecting group, or Y$_3$ or Y$_4$ together are acetal, ketal, or 1,1,3,3-tetraisopropylsiloxanediyl;
- T is -OY$_5$; and
- Y$_5$, together with the oxygen atom to which it is bound, is an ester, carbonate, carbamate, sulfonate, or ether hydroxyl protecting group.

13. The method of claim 12, wherein, in the compound of formula (II), Y$_1$ is pivaloyl, acetyl, benzoyl, p-bromobenzoyl, p-methoxybenzoyl, 1-naphthoyl, 2-naphthoyl, o-phthaloyl, benzyl, p-methoxybenzyl, triphenylmethyl, tri(C1-C6alkyl)silyl, tri(C6-C10 aryl or C1-C6 heteroaryl)silyl, di(C6-C10 aryl or C1-C6 heteroaryl)(C1-C6 alkyl)silyl, or (C6-C10 aryl or C1-C6 heteroaryl)di (C1-C6 alkyl)silyl.

14. The method of claim 12, wherein, in the compound of formula (II), Y$_3$ and Y$_4$ are each independently tri(C1-C6 alkyl)silyl, tri(C6-C10 aryl or C1-C6 heteroaryl)silyl, di(C6-C10 aryl or C1-C6 heteroaryl)(C1-C6 alkyl)silyl, or (C6-C10 aryl or C1-C6 heteroaryl)di(C1-C6 alkyl)silyl, or Y$_3$ and Y$_4$ are together di(C1-C6alkyl)silylene.

15. The method of claim 12, wherein, in the compound of formula (II), Y$_5$ is acetyl, benzoyl, p-bromobenzoyl, p-methoxybenzoyl, 1-naphthoyl, 2-naphthoyl, or o-phthaloyl.

16. The method of claim 1, wherein the compound of formula (II) has formula (IIc):

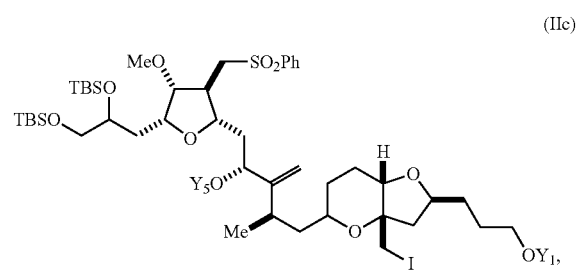

wherein Y$_1$ and Y$_5$ are as follows:

| Y$_1$ | Y$_5$ |
|---|---|
| H | H |
| benzoyl | benzoyl |
| p-bromobenzoyl | p-bromobenzoyl |
| pivaloyl | H |
| pivaloyl | acetyl |
| pivaloyl | benzoyl |
| 2-naphthoyl | H |
| 2-naphthoyl | 2-naphthoyl |
| 1-naphthoyl | H |
| 1-naphthoyl | 1-naphthoyl |
| p-methoxybenzoyl | H |
| p-methoxybenzoyl | p-methoxybenzoyl |
| o-phthaloyl or salt thereof | H. |

17. The method of claim 1, wherein the compound of formula (II) is:

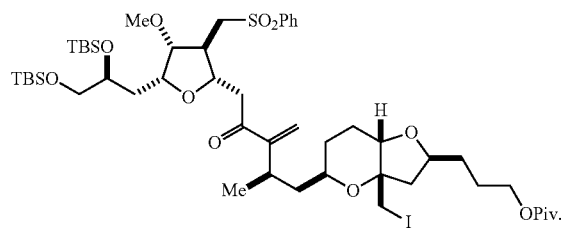

AD

18. The method of claim 1, wherein the compound of formula (III) has formula (IIIa):

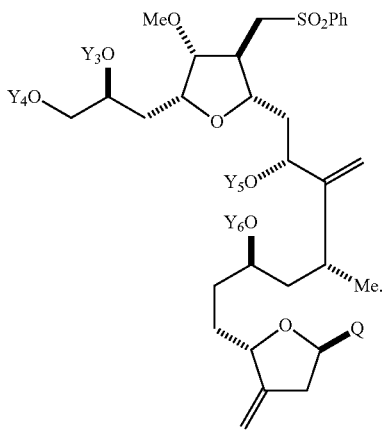

(IIIa)

19. The method of claim 18, wherein, in the compound of formula (III), Q is —(CH$_2$)$_3$OY$_1$;
   Y$_1$, together with the oxygen atom to which it is bound, is an ester, carbonate, carbamate, sulfonate, or ether hydroxyl protecting group;
   Y$_3$ and Y$_4$ are each, independently and together with the oxygen atom to which it is bound, an ester, carbonate, carbamate, sulfonate, or ether hydroxyl protecting group, or Y$_3$ and Y$_4$ together with the oxygen atoms to which they are bound are a cyclic carbonate, cyclic boronate, or cyclic silylene hydroxyl protecting group, or Y$_3$ and Y$_4$ together are acetal, ketal, or 1,1,3,3-tetraisopropylsiloxanediyl; and
   Y$_5$, together with the oxygen atom to which it is bound, is an ester, carbonate, carbamate, sulfonate, or ether hydroxyl protecting group.

20. The method of claim 19, wherein, in the compound of formula (III), Y$_1$ is pivaloyl, acetyl, benzoyl, p-bromobenzoyl, p-methoxybenzoyl, 1-naphthoyl, 2-naphthoyl, o-phthaloyl, benzyl, p-methoxybenzyl, triphenylmethyl, tri(C1-C6 alkyl)silyl, tri(C6-C10 aryl or C1-C6 heteroaryl)silyl, di(C6-C10 aryl or C1-C6 heteroaryl)(C1-C6 alkyl)silyl, or (C6-C10 aryl or C1-C6 heteroaryl)di(C1-C6 alkyl)silyl.

21. The method of claim 19, wherein, in the compound of formula (III), Y$_3$ and Y$_4$ are each independently tri(C1-C6 alkyl)silyl, tri(C6-C10 aryl or C1-C6 heteroaryl)silyl, di(C6-C10 aryl or C1-C6 heteroaryl)(C1-C6 alkyl)silyl, or (C6-C10 aryl or C1-C6 heteroaryl)di(C1-C6 alkyl)silyl, or Y$_3$ and Y$_4$ are together di(C1-C6)alkylsilylene.

22. The method of claim 19, wherein, in the compound of formula (III), Y$_5$ is acetyl, benzoyl, p-bromobenzoyl, p-methoxybenzoyl, 1-naphthoyl, 2-naphthoyl, or o-phthaloyl.

23. The method of claim 18, wherein, in the compound of formula (III), Y$_5$ is H or a hydroxyl protecting group.

24. The method of claim 18, wherein, in the compound of formula (III), Y$_6$ is H.

25. The method of claim 18, wherein, in the compound of formula (III), -OY$_6$ is a leaving group.

26. The method of claim 25, wherein, in the compound of formula (III), -OY$_6$ is (C1-C6)alkylsulfonate, (C6-C10 aryl or C1-C6 heteroaryl)sulfonate, (C6-C15)aryl(C1-C6)alkylsulfonate, or (C1-C6)heteroaryl(C1-C6)alkylsulfonate.

27. The method of claim 26, wherein, in the compound of formula (III), -OY$_6$ is mesylate, toluenesulfonate, isopropylsulfonate, phenylsulfonate, or benzylsulfonate.

28. The method of claim 18, wherein the compound of formula (III) is

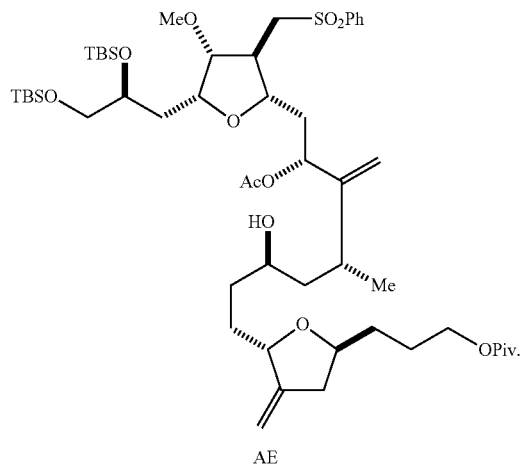

AE

* * * * *